United States Patent
Takahashi

(10) Patent No.: US 6,586,554 B1
(45) Date of Patent: Jul. 1, 2003

(54) POLYARYLENE AND METHOD FOR PRODUCTION THEREOF

(75) Inventor: Tamotsu Takahashi, Sapporo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 10/030,945

(22) PCT Filed: Apr. 24, 2000

(86) PCT No.: PCT/JP00/02659

§ 371 (c)(1),
(2), (4) Date: Jan. 15, 2002

(87) PCT Pub. No.: WO01/05864

PCT Pub. Date: Jan. 25, 2001

(30) Foreign Application Priority Data

Jul. 15, 1999 (JP) ............................................ 11-201954

(51) Int. Cl.$^7$ ........................ C08G 61/10; C08F 283/00
(52) U.S. Cl. ....................... 528/86; 528/166; 525/328.1; 525/534
(58) Field of Search ................. 528/86, 166; 525/328.1, 525/534

(56) References Cited

FOREIGN PATENT DOCUMENTS

JP          9-309945          12/1997

Primary Examiner—Duc Truong

(74) Attorney, Agent, or Firm—Oblon, Spivak, McClelland, Maier & Neustadt, P.C.

(57) ABSTRACT

This invention provides polyarylenes having a recurring unit shown by formula (I) or (II) below and a process for production thereof as well as these monomers: (wherein $Ar^1$ and $Ar^2$ are an arylene; $R^1$ and $R^2$ are $C_1$–$C_{20}$ hydrocarbon group, etc.; $A^1$ and $A^2$ are $C_1$–$C_{20}$ hydrocarbon group, etc.; and n is an integer of 2 or more);

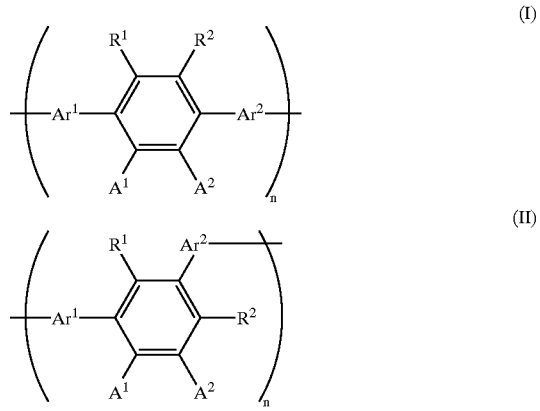

(wherein $Ar^1$ and $Ar^2$ are an arylene; $R^1$ and $R^2$ are $C_1$–$C_{20}$ hydrocarbon group, etc.; $A^1$ and $A^2$ are $C_1$–$C_{20}$ hydrocarbon group, etc.; and n is an integer of 2 or more) The polyarylenes of the invention find extensive applications as electrically conductive resins. The polyarylenes can be used also as resin compositions in a variety of formed shapes.

19 Claims, No Drawings

POLYARYLENE AND METHOD FOR PRODUCTION THEREOF

FIELD OF THE INVENTION

The present invention relates to a polyarylene, a teraryl and a teraryl precursor, as well as to a method for producing a polyarylene. More particularly, the invention relates to a polyarylene having terarylene recurring units on the backbone and a method for production thereof.

BACKGROUND ART

Polyarylenes are of interest because the arylene group as a recurring unit has excellent thermal and chemical stability. Also, polyarylenes have been attracting considerable attention to their peculiar physical properties because of the advanced π-electron conjugated system.

A variety of applications as, e.g., conductive polymers are anticipated for polyarylenes. Polyphenylene s may also be either oxidized or reduced so that anions or cations are doped to form p type or n type semiconductors. Utilizing the property, it is also expected to apply poly(p-phenylene) to electrode materials or apply as display elements using a change in absorbance upon oxidation or reduction.

Moreover, polyarylenes are expected to be applicable to macro molecule light emitting elements. In this field, elements called macro molecule light emitting electrochemical elements (LEC) have been proposed lately and drawn attention in view of their high luminous efficiency. The structure includes two electrodes, between which a electrically conductive polymer material and a polymer membrane comprising polyethylene oxide having ionic conductivity and a substrate salt are inserted. It is assumed that the principle of working mechanism is based on the input of positive and negative charges from the electrodes and the transfer of both positive and negative ions of the substrate salt as a dopant, whereby a p-n junction would be formed in the membrane. If an ionic conductivity is further imparted to conductive polymer substances having an electronic conductivity, such light emitting elements will be manufactured using a sole material, not with the composite membrane mentioned above, resulting in a great advantage in manufacturing steps.

Processes for manufacturing polyarylenes such as polyphenylene have been hitherto limited. For manufacturing polyphenylenes, for example, oxidative cation polymerization called the Kovacic process, which is polycondensation using benzene as a monomer, is known. As is described in P. Kovacic, et al., Chem. Rev., 1987, 87, 357–379, an oxidizing agent such as cupric chloride and a Lewis acid catalyst such as aluminum chloride are employed to form insoluble polyphenylene of uncertain structure. It is reported that polyphenylene formed by oxidation of benzene is branched polyphenylene with a low molecular weight.

Further processes are proposed for manufacturing polyarylenes, which include electrochemical oxidative polymerization (a process using a cupric chloride-lithium aluminum hexafluoride-based electrolyte and applying a voltage between electrodes to produce a polymer on the electrodes); as polycondensation of substituted benzene derivatives, Wurtz-Fittig reaction (a process involving condensation of a dihalogenobenzene with an alkali metal) Ullmann reaction (a process involving condensation of diiodobenzene with a metal copper), Grignard reaction called Yamamoto method (a process involving condensation of a dihalogenobenzene Grignard derivative with a nickel chloride-bipyridyl complex), diazonium coupling (a process involving condensation of a diazonium derivative with sodium nitrite/hydrochloric acid followed by treatment with copper chloride); as processes via precursors, dehydration of cyclohexadiene polymer, a bio-engineering method (which comprises oxidizing benzene with bacteria to synthesize 5,6-dihydroxycyclohexane-1,3-diene, subjecting the carbonic acid ester of the diene to radical polymerization and then heating the resulting intermediate polymer to effect synthesis); and so on.

DISCLOSURE OF THE INVENTION

However, polyarylenes having terarylene recurring units are extremely rarely known. In these polyarylenes, it has been sought to introduce substituents freely into the central arylene of the terarylene unit and modify the terarylene in various ways.

For example, Japanese Patent Unexamined Publication (Laid-open) No. 9-309945 discloses polyphenylene copolymers. According to this patent publication, polyphenylene copolymers are synthesized using various types of monoarylenes as recurring units.

Now, an object of the present invention is to provide polyarylenes containing a terarylene as the recurring unit.

In a first aspect of the present invention, there are provided polyarylenes comprising a recurring unit represented by formula (I) or (II) below:

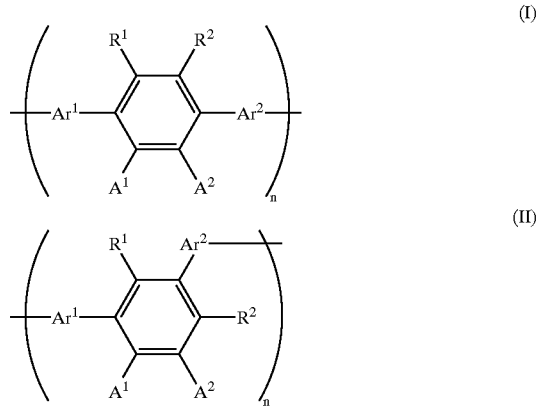

(wherein:
$Ar^1$ and $Ar^2$ which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group)

provided that, in the recurring unit of formula (I), $R^1$ and $R^2$ may form together a $C_4$–$C_{20}$ saturated or unsaturated ring which may be intervened by an oxygen atom and may be substituted;

$A^1$ and $A^2$, which may be the same or different, each represents hydrogen atom; a $C_1$–$C_{20}$ hydrocarbon group which may optionally be substituted; a $C_1$–$C_{20}$ alkoxy group which may optionally be substituted; a $C_6$–$C_{20}$ aryloxy group which may optionally be substituted; a $C_6$–$C_{20}$ alkylaryloxy group which may optionally be substituted; a $C_1$–$C_{20}$ alkoxycarbonyl group which may optionally be substituted; a $C_6$–$C_{20}$ aryloxycarbonyl group which may optionally be substituted; cyano group (—CN); carbamoyl group (—C(=O)NH$_2$); a haloformyl group (—C(=O)—X, wherein X is a halogen atom); or formyl group (—C(=O)—H); and, n is an integer of 2 or more).

In the present invention, preferably, $A^1$ and $A^2$, which may be the same or different, each represents independently a phenylene group which may optionally be substituted.

Also, the recurring unit is preferably a recurring unit shown by formula (I) described above, wherein $R^1$ and $R^2$ may form together a $C_4$–$C_{20}$ saturated or unsaturated ring which may be intervened by an oxygen atom and may optionally be substituted.

Furthermore, the $C_1$–$C_{20}$ hydrocarbon group is preferably a linear or branched $C_1$–$C_{20}$ alkyl group, a linear or branched $C_2$–$C_{20}$ alkenyl group, a linear or branched $C_2$–$C_{20}$ alkynyl group, a linear or branched $C_3$–$C_{20}$ allyl group, a linear or branched $C_4$–$C_{20}$ alkadienyl group, a linear or branched $C_4$–$C_{20}$ polyenyl group, a $C_6$–$C_{18}$ aryl group, a $C_6$–$C_{20}$ alkylaryl group, a $C_6$–$C_{20}$ arylalkyl group, a $C_4$–$C_{20}$ cycloalkyl group, or a $C_4$–$C_{20}$ cycloalkenyl group.

In a further aspect of the invention, there is provided a polyarylene comprising a recurring unit represented by the formula (I) below:

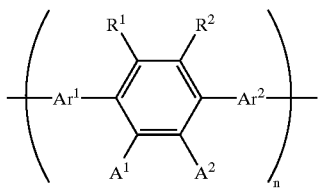

(I)

(wherein:
Ar$^1$ and Ar$^2$, which may be the same or different, each represents independently a paraarylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si(R$^3$)(R$^4$)(R$^5$) (wherein R$^3$, R$^4$ and R$^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the recurring unit of formula (I), $R^1$ and $R^2$ may form together a $C_4$–$C_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; an alkoxycarbonyl group which may be substituted; a $C_6$–$C_{20}$ aryloxycarbonyl group which may be substituted; cyano group (—CN); carbamoyl group (—C(=O)NH$_2$); a haloformyl group (—C(=O)—X, wherein X is a halogen atom); or formyl group (—C(=O)—H); and, n is an integer of 2 or more).

In the present invention, preferably, $A^1$ and $A^2$, which may be the same or different, each represents independently a paraphenylene group which may optionally be substituted.

Also, the recurring unit is preferably a recurring unit shown by formula (I) described above, wherein $R^1$ and $R^2$ form together a $C_4$–$C_{20}$ saturated or unsaturated ring which may be intervened by an oxygen atom and may be substituted.

Furthermore, the $C_1$–$C_{20}$ hydrocarbon group is preferably a linear or branched $C_1$–$C_{20}$ alkyl group, a linear or branched $C_2$–$C_{20}$ alkenyl group, a linear or branched $C_2$–$C_{20}$ alkynyl group, a linear or branched $C_3$–$C_{20}$ allyl group, a linear or branched $C_4$–$C_{20}$ alkadienyl group, a linear or branched $C_4$–$C_{20}$ polyenyl group, a $C_6$–$C_{18}$ aryl group, a $C_6$–$C_{20}$ alkylaryl group, a $C_6$–$C_{20}$ arylalkyl group, a $C_4$–$C_{20}$ cycloalkyl group, or a $C_4$–$C_{20}$ cycloalkenyl group.

In a further aspect of the invention, there is provided a resin composition comprising the polyarylene described above and a synthetic organic polymer.

In a further aspect of the invention, there is provided a teraryl shown by formula (III) or (IV) below:

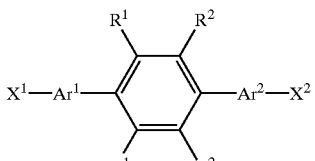

(III)

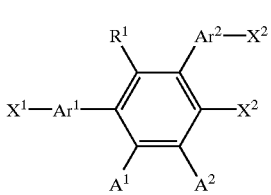

(IV)

(wherein
Ar$^1$ and Ar$^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si(R$^3$)(R$^4$)(R$^5$) (wherein R$^3$, R$^4$ and R$^5$, which may be the same or different, each represents independently a $C_1$–$C_{20}$ alkyl group, a $C_6$–$C_{20}$ aryla-lkyl group, a $C_1$–$C_{20}$ alkoxy group or a $C_6$–$C_{20}$ aryla-lkyloxy group)

provided that, in the recurring unit of formula (III), $R^1$ and $R^2$ may form together a $C_4$–$C_{20}$ saturated or unsatur-ated ring which may be intervened by an oxygen atom and may optionally be substituted;

$A^1$ and $A^2$, which may be the same or different, each represents independently hydrogen atom; a $C_1$–$C_{20}$ hydrocarbon group which may optionally be substituted; a $C_1$–$C_{20}$ alkoxy group which may optionally be substituted; a $C_6$–$C_{20}$ aryloxy group which may optionally be substituted; a $C_6$–$C_{20}$ alkylaryloxy group which may optionally be substituted; a $C_1$–$C_{20}$ alkoxycarbonyl group which may optionally be substituted; a $C_6$–$C_{20}$ aryloxycarbonyl group which may optionally be substituted; cyano group (—CN); carbamoyl group (—C(=O)NH$_2$); a haloformyl group (—C(=O)—X, wherein X is a halogen atom); or formyl group (—C(=O)—H); and, $X^1$ and $X^2$, which may be the same or different, each represents independently a leaving group).

In a still further aspect of the present invention, there is provided a process for producing a polyarylene of formula (I) or (II) below:

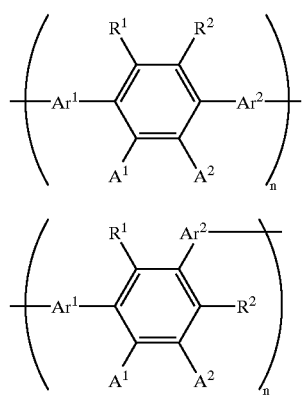

(wherein:
Ar$^1$ and Ar$^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si(R$^3$)(R$^4$)(R$^5$) (wherein R$^3$, R$^4$ and R$^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the recurring unit of formula (I), $R^1$ and $R^2$ may form together a $C_4$–$C_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may optionally be substituted; a $C_1$–$C_{20}$ alkoxy group which may optionally be substituted; a $C_6$–$C_{20}$ aryloxy group which may optionally be substituted; a $C_6$–$C_{20}$ alkylaryloxy group which may optionally be substituted; a $C_1$–$C_{20}$ alkoxycarbonyl group which may optionally be substituted; a $C_6$–$C_{20}$ aryloxycarbonyl group which may optionally be substituted; cyano group (—CN); carbamoyl group (—C(=O)NH$_2$); a haloformyl group (—C(=O)—X, wherein X is a halogen atom); or formyl group (—C(=O)—H); and, n is an integer of 2 or more), which comprises polymerizing a teraryl represented by formula (III) or (IV) below:

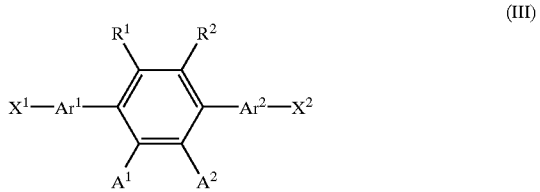

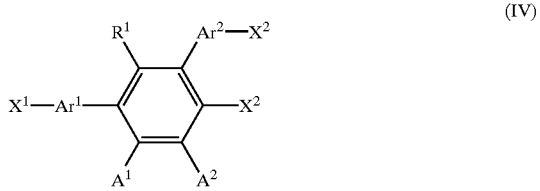

(wherein
Ar$^1$, Ar$^2$, R$^1$, R$^2$, A$^1$ and A$^2$ have the same significance as defined above; and,
$X^1$ and $X^2$, which may be the same or different, each represents independently a leaving group).

In a further aspect of the present invention, there is provided a process for producing a teraryl, which comprises reacting a metallacyclopentadiene represented by formula (V) or (VI) below:

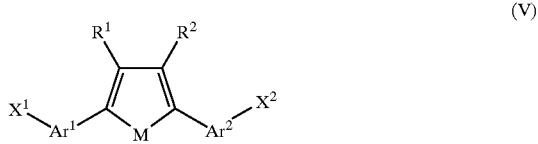

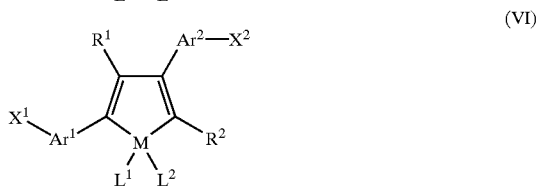

(wherein:
M is a metal from Groups III–V or the lanthanide series of the Periodic Table;
L$^1$ and L$^2$, which may be the same or different, each represents independently an anionic ligand, provided that L$^1$ and L$^2$ may be crosslinked;
Ar$^1$ and Ar$^2$, which may be the same or different, each represents independently an arylene having 4 to 18 carbon atoms, which may be substituted and may contain 1 to 5 nitrogen atoms;
R$^1$ and R$^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si(R$^3$)(R$^4$)(R$^5$) (wherein R$^3$, R$^4$ and R$^5$, which may be the same or different, each represents a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group).
provided that, in the metallacyclopentadiene shown by formula (V), R$^1$ and R$^2$ may form together a $C_4$–$C_{20}$ saturated or unsaturated ring which may be intervened by an oxygen atom and may optionally be substituted; and, $X^1$ and $X^2$, which may be the same or different, each represents independently a leaving group);

with an alkyne derivative represented by formula (VII) below:

(VII)

(wherein;

$A^{1a}$ and $A^{2a}$, which may be the same or different, each represents independently hydrogen atom; a $C_1$–$C_{20}$ hydrocarbon group which may optionally be substituted; a $C_1$–$C_{20}$ alkoxy group which may optionally be substituted; a $C_6$–$C_{20}$ aryloxy group which may optionally be substituted; a $C_6$–$C_{20}$ alkylaryloxy group which may optionally be substituted; a $C_1$–$C_{20}$ alkoxycarbonyl group which may optionally be substituted; a $C_6$–$C_{20}$ aryloxycarbonyl group which may optionally be substituted; a $C_6$–$C_{20}$ aryloxy group which may optionally be substituted; a $C_6$–$C_{20}$ alkylaryloxy group which may optionally be substituted; or cyano group (—CN);

to produce a teraryl represented by formula (IIIa) or (IVa) below:

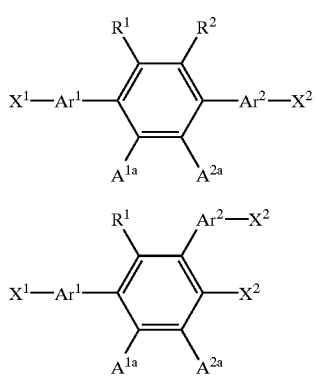

(wherein each of $Ar^1$, $Ar^2$, $R^1$, $R^2$, $A^{1a}$, $A^{2a}$, $X^1$ and $X^2$ has the same significance as defined above).

In the present invention, preferably, M is a metal from Group IV or the lanthanide series of the Periodic Table; the anionic ligand is non-localized cyclic $\eta^5$-coordination type ligand, a $C_1$–$C_{20}$ alkoxy group, a $C_6$–$C_{20}$ aryloxy group or a dialkylamide group.

The non-localized cyclic $\eta^5$-coordination type ligand described above is preferably a cyclopentadienyl, indenyl, fluorenyl or azulenyl group, which may be substituted.

Furthermore, the reaction preferably proceeds in the presence of a compound containing a metal from Groups IX–XV of the Periodic Table.

In a still further aspect of the invention, there is provided a process for producing a polyarylene, which comprises reacting a metallacyclopentadiene represented by formula (V) or (VI) below:

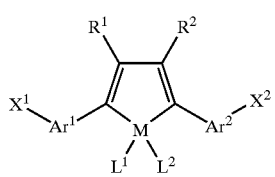

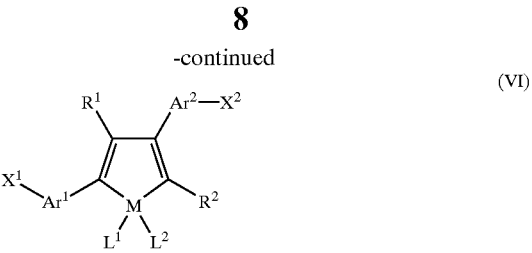

(wherein:

$Ar^1$ and $Ar^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the metallacyclopentadiene shown by formula (V), $R^1$ and $R^2$ may form together a $C_4$–$C_{20}$ saturated or unsaturated ring which may be intervened by an oxygen atom and may be substituted;

M is a metal from Groups III–V or the lanthanide series of the Periodic Table;

$L^1$ and $L^2$, which may be the same or different, each represents independently an anionic ligand, provided that $L^1$ and $L^2$ may be crosslinked; and, $X^1$ and $X^2$, which may be the same or different, each represents independently a leaving group);

with an alkyne derivative represented by formula (VII) below:

(VII)

(wherein;

$A^{1a}$ and $A^{2a}$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; $C_6$–$C_{20}$ alkylaryloxy group which may be substituted; $C_1$–$C_{20}$ alkoxycarbonyl group which may be substituted; a $C_6$–$C_{20}$ aryloxycarbonyl group which may be substituted; or cyano group (—CN); to produce a teraryl represented by formula (IIIa) or (IVa) below:

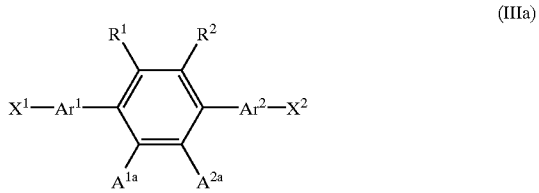

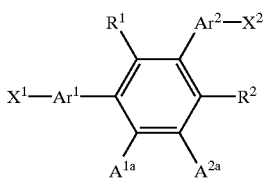

(IVa)

(wherein each of $Ar^1$, $Ar^2$, $R^1$, $R^2$, $A^{1a}$, $A^{2a}$, $X^1$ and $X^2$ has the same significance as defined above); and polymerizing the resulting teraryl to produce the polyarylene represented by formula (Ia) or (IIa) below:

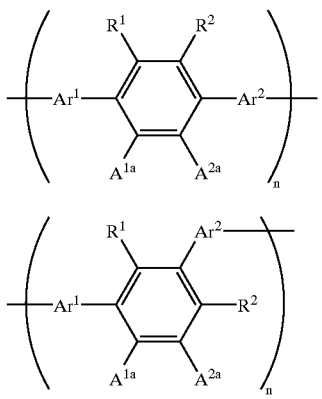

(Ia)

(IIa)

(wherein each of $Ar^1$, $Ar^2$, $R^1$, $R^2$, $A^{1a}$ and $A^{2a}$ has the same significance as defined above; and n is an integer of 2 or more).

In the present invention, preferably, M is a metal from Group IV or the lanthanide series of the Periodic Table; the anionic ligand is non-localized cyclic $\eta^5$-coordination type ligand, a $C_1$–$C_{20}$ alkoxy group, a $C_6$–$C_{20}$ aryloxy group or a dialkylamide group.

The non-localized cyclic $\eta^5$-coordination type ligand described above is preferably a cyclopentadienyl, indenyl, fluorenyl or azulenyl group, which may be substituted.

Furthermore, the reaction preferably proceeds in the presence of a compound containing a metal from Groups IX–XV of the Periodic Table.

In a still further aspect of the present invention, here is provided a metallacyclopentadiene represented by formula (V) or (VI) below:

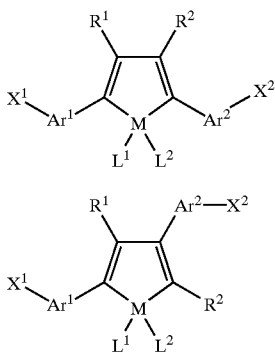

(V)

(VI)

(wherein:

M is a metal from Groups III–V or the lanthanide series of the Periodic Table;

$L^1$ and $L^2$, which may be the same or different, each represents independently an anionic ligand, provided that $L^1$ and $L^2$ may be crosslinked;

$Ar^1$ and $Ar^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ aralkyl group, a $C_1$–$C_{20}$ alkoxy group or a $C_6$–$C_{20}$ aralkyloxy group);

provided that, in the metallacyclopentadiene shown by formula (V), $R^1$ and $R^2$ may form together a $C_4$–$C_{20}$ saturated or unsaturated ring which may be intervened by an oxygen atom and may be substituted; and, $X^1$ and $X^2$, which may be the same or different, each represents independently a leaving group).

PREFERRED EMBODIMENTS OF THE INVENTION

In one aspect of the present invention, the polyarylenes represented by formula (I) or (II) described above are provided.

$Ar^1$ and $Ar^2$, which may be the same or different, each represents independently an arylene having 4 to 18 carbon atoms, which may be substituted and may contain 1 to 5 nitrogen atoms. $Ar^1$ and $Ar^2$ are preferably 5- to 18-membered, more preferably, 6- to 14-membered. Where the arylene contains nitrogen atoms, the number of nitrogen atoms is preferably 1 to 3, more preferably 1 or 2.

The arylene may be a carbon ring or may be a heterocyclic ring containing 1 to 5 nitrogen atoms. The arylene may be a monocyclic ring or a condensed ring. Examples of the arylene include phenylenes (1,3- and 1,4-phenylenes), 5-amino-1,3-phenylene, 4-benzoyl-1,3-phenylene, 5-benzoyl-1,3-phenylene, 2-benzoyl-1,4-phenylene, 4,4'-biphenyldiyl, 2-carboxy-methyl-1,4-phenylene, 4-carboxymethyl-1,3-phenylene, 5-carboxymethyl-1,3-phenylene, 1,3-naphthalenediyl, 1,4-naphthalenediyl, 5-phenoxy-1,3-phenylene, 2-phenyl-1,3-phenylene, 4-phenyl-1,3-phenylene, 5-phenyl-1,3-phenylene, 2-phenyl-1,4-phenylene, 2,6-pyridinediyl, 2,4-pyridinediyl, 3,5-pyridinediyl, 3,6-pyridinediyl, 5,8-quinolinediyl, 2,4-toluenediyl, 2,5-xylenediyl and so on. As isomers of the arylenes other than those at the 1,3- and 1,4-positions, which are not described above, there are, e.g., 2,4-quinolinediyl, 2,5-quinolinediyl, 2,6-quinolinediyl, and the like. Preferred examples of the arylenes are phenylene, naphthalenediyl and pyridinediyl, which may optionally be substituted, and more preferably, phenylene and naphthalenediyl which may optionally be substituted.

Examples of substituents on the arylenes shown by $Ar^1$ and $Ar^2$ are a $C_1$–$C_{20}$ hydrocarbon group, a $C_1$–$C_{20}$ alkoxy group, a $C_6$–$C_{20}$ aryloxy group, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group)

The substituents on the arylenes are not limited to those given above, so long as they are substituents that can be introduced into the arylenes prior to or after the formation of a teraryl as the monomer, and unless they interfere with the reaction. Furthermore, by introducing an appropriate protecting group, various substituents can be introduced into the arylenes by publicly known reactions for ordinary aromatic compounds, for example, through nucleophilic substitution.

$R^1$ and $R^2$, which may be the same or different, each represents independently a $C_1$–$C_{20}$ hydrocarbon group which may optionally be substituted, a $C_1$–$C_{20}$ alkoxy group which may optionally be substituted, a $C_6$–$C_{20}$ aryloxy group which may optionally be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group)

In the specification, the $C_1$–$C_{20}$ hydrocarbon group may be a saturated or unsaturated acyclic hydrocarbon or a saturated or unsaturated cyclic hydrocarbon. Where the $C_1$–$C_{20}$ hydrocarbon group is acyclic, the group may be linear or branched. Examples of the $C_1$–$C_{20}$ hydrocarbon group include a $C_1$–$C_{20}$ alkyl group, a $C_2$–$C_{20}$ alkenyl group, a $C_2$–$C_{20}$ alkynyl group, a $C_3$–$C_{20}$ allyl group, a $C_4$–$C_{20}$ alkadienyl group, a $C_4$–$C_{20}$ polyenyl group, a $C_6$–$C_{18}$ aryl group, a $C_6$–$C_{20}$ alkylaryl group, a $C_6$–$C_{20}$ arylalkyl group, a $C_4$–$C_{20}$ cycloalkyl group, and a $C_4$–$C_{20}$ cycloalkenyl group.

Examples of the alkyl group which is useful to practice the invention include, but are not limited to, methyl, ethyl, propyl, n-butyl, t-butyl, dodecanyl, trifluoromethyl, perfluoro-n-butyl, 2,2,2-trifluoroethyl, benzyl, 2-phenoxyethyl, etc.

Examples of the aryl group which is useful to practice the invention include, but are not limited to, phenyl, 2-tolyl, 3-tolyl, 4-tolyl, naphthyl, biphenyl, 4-phenoxyphenyl, 4-fluorophenyl, 3-carbomethoxyphenyl, 4-carbomethoxyphenyl, etc.

Examples of the alkoxy group which is useful to practice the invention include, but are not limited to, methoxy, ethoxy, 2-methoxyethoxy, t-butoxy, etc. Examples of the aryloxy group which is useful to practice the invention include, but are not limited to, phenoxy, naphthoxy, phenylphenoxy, 4-methylphenoxy, etc.

Examples of the amine group which is useful to practice the invention include, but are not limited to, amino, dimethylamino, methylamino, methylphenylamino, phenylamino, etc.

Examples of the group shown by formula: —Si($R^3$)($R^4$)($R^5$) include, but are not limited to, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, methylmethoxyphenyl, etc.

Substitutents may be introduced into the $C_1$–$C_{20}$ hydrocarbon group, $C_1$–$C_{20}$ alkoxy group, and $C_6$–$C_{20}$ aryloxy group. Examples of the substituents are a halogen atom, hydroxy group, amino group, etc.

In the recurring unit shown by formula (I), however, $R^1$ and $R^2$ may form together a $C_4$–$C_{20}$ saturated or unsaturated ring which may be intervened by an oxygen atom and may be substituted. Preferably, The ring is a 4- to 16-membered ring, more preferably a 4- to 12-membered ring. The ring may optionally be substituted with substituents such as a $C_1$–$C_{20}$ hydrocarbon group, a $C_1$–$C_{20}$ alkoxy group, a $C_6$–$C_{20}$ aryloxy group, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group), etc.

$A^1$ and $A^2$, which may be the same or different, each represents independently hydrogen atom; a $C_1$–$C_{20}$ hydrocarbon group which may optionally be substituted; a $C_1$–$C_{20}$ alkoxy group which may optionally be substituted; a $C_6$–$C_{20}$ aryloxy group which may optionally be substituted; a $C_6$–$C_{20}$ alkylaryloxy group which may optionally be substituted; a $C_1$–$C_{20}$ alkoxycarbonyl group which may optionally be substituted; a $C_6$–$C_{20}$ aryloxycarbonyl group which may optionally be substituted; cyano group (—CN); carbamoyl group (—C(=O)NH$_2$); a haloformyl group (—C(=O)—X, wherein X is a halogen atom); or formyl group (—C(=o)—H). The $C_1$–$C_{20}$ hydrocarbon group, the $C_1$–$C_{20}$ alkoxy group which may optionally be substituted, the $C_6$–$C_{20}$ aryloxy group which may optionally be substituted and the amino group are the same as those given for $R^1$ and $R^2$.

Examples of the alkoxycarbonyl group which is useful to practice the invention include, but are not limited to, methoxycarbonyl, ethoxycarbonyl, 2-methoxyethoxycarbonyl, t-butoxycarbonyl, etc.

Examples of the aryloxycarbonyl group which is useful to practice the invention include, but are not limited to, phenoxycarbonyl, naphthoxycarbonyl, phenylphenoxycarbonyl, 4-methylphenoxycarbonyl, etc.

Carbamoyl group (—C(=O)NH$_2$), the haloformyl group (—C(=O)—X, wherein X is a halogen atom), formyl group (—C(=O)—H) or the like can be mutually converted into cyano group or an alkoxycarbonyl group.

The polyarylenes of the present invention may also be copolymers. In addition to the terarylene recurring units described above, the polyarylenes may contain, e.g., one or more other recurring units. The other recurring unit may be an arylene. Examples of the arylene include phenylenes (1,3- and 1,4-phenylenes), 5-amino-1,3-phenylene, 4-benzoyl-1,3-phenylene, 5-benzoyl-1,3-phenylene, 2-benzoyl-1,4-phenylene, 4,4'-biphenyldiyl, 2-carboxymethyl-1,4-phenylene, 4-carboxymethyl-1,3-phenylene, 5-carboxymethyl-1,3-phenylene, 1,3-naphthalenediyl, 1,4-naphthalenediyl, 5-phenoxy-1,3-phenylene, 2-phenyl-1,3-phenylene, 4-phenyl-1,3-phenylene, 5-phenyl-1,3-phenylene, 2-phenyl-1,4-phenylene, 2,6-pyridinediyl, 2,4-pyridinediyl, 3,5-pyridinediyl, 3,6-pyridinediyl, 5,8-quinolinediyl, 2,4-toluenediyl, 2,5-xylenediyl and so on. As isomers of the arylenes other than those at the 1,3- and 1,4-positions, which are not described above, there are, e.g., 2,4-quinolinediyl, 2,5-quinolinediyl, 2,6-quinolinediyl, and the like.

In other aspect of the present invention, there is provided a resin composition, e.g., a blend, comprising the polyarylene and a synthetic organic polymer. For example, there is provided a resin composition comprising 1 to 99 wt % of the polyarylene and 99 to 1 wt % of the synthetic organic polymer. There is also provided 10 to 90 wt %of the polyarylene and 90 to 10 wt % of the synthetic organic polymer.

The synthetic organic polymer includes a thermoplastic polymer, a thermosetting polymer, engineering plastics, etc.

The synthetic organic polymer may also be a copolymer. Examples of the thermoplastic polymer are polyolefin such as polyethylene, polypropylene, polycycloolefin, ethylene-propylene copolymer, etc.; polyvinyl chloride, polyvinylidene chloride, polyvinyl acetate, polyacrylic acid, polymethacrylic acid, polystyrene, polyamide, polyester, polycarbonate, etc. Examples of the thermosetting polymer are phenol resin, urea resin, melamine resin, alkyd resin, unsaturated polyester resin, epoxy resin, silicone resin and polyurethane resin. Examples of the engineering plastics include polyimide, polyphenylene oxide, polysulfone, etc. The synthetic organic polymer may be synthetic rubber such as styrene-butadiene, etc., or fluorine resin such as polytetrafluoroethylene, etc.

The resin composition may also contain a variety of additives. Examples of the additives are plasticizers, antistatic agents, coloring agents, etc. The resin composition may further contain reinforcing agents such as glass fibers, carbon fibers, etc.

The polyarylene or resin composition in accordance with the present invention can be prepared into the shape of fibers, films or sheets using methods publicly known to one skilled in the art. Examples of such methods include, but are not limited to, melt spinning, spinning from a solution, dry jet wet spinning, extrusion, flow casting and molding. The fibers, films or sheets are further processed by means of calender molding, embossing, forming or other means publicly known to one skilled in the art.

In a still further aspect of the present invention, there is provided a teraryl represented by formula (III) or (IV). In formula (III) or (IV), $Ar^1$, $Ar^2$, $R^1$, $R^2$, $A^1$ and $A^2$ have the same significance as defined above.

$X^1$ and $X^2$, which may be the same or different, each represents independently a leaving group. Examples of the leaving group are a halogen atom such as F, Cl, Br or I, p-toluenesulfonyl group, etc., with particular preference being Br.

In a still further aspect of the present invention, there is provided a process for producing the polyarylene represented by formula (I) or (II) described above. This reaction is shown by the following equation:

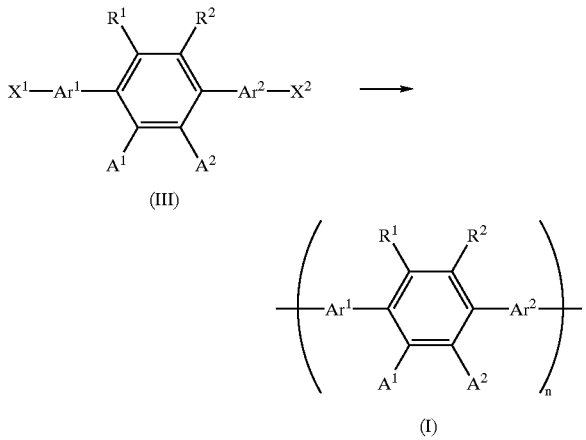

(wherein $Ar^1$, $Ar^2$, $R^1$, $R^2$, $A^1$, $A^2$, $X^1$ and $X^2$ have the same significance as defined above);

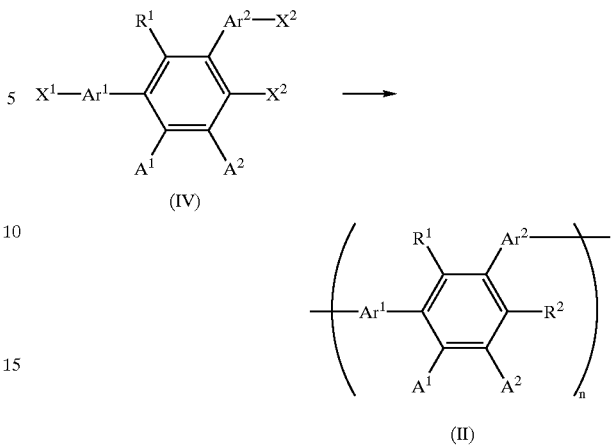

(wherein $Ar^1$, $Ar^2$, $R^1$, $R^2$, $A^1$, $A^2$, $X^1$ and $X^2$ have the same significance as defined above).

Polymerization is carried out by coupling monomers through removal of the leaving groups $X^1$ and $X^2$ with a reducing agent. As the reducing agent, e.g., metals from Groups I–XIV of the Periodic Table can be widely employed. Examples of the reducing agent include metals from Group I of the Periodic Table such as lithium or sodium; metals from Group II such as magnesium; metals from Group XI such as copper; and metals from Group XII such as zinc.

The polymers of the present invention can be formed by polymerization of monomers described above through reductive coupling using a nickel (0) compound described in T. Kanbara, T. Kushida, N. Saito, I. Kuwajima, K. Kubota and T. Yamamoto, Chemistry Letters, 1992, 583–586, or through nickel catalyst-reductive coupling described in U.S. Pat. Nos. 5,227,457 or 5,241,044.

That is, where a mild reducing agent such as magnesium or zinc is used, an organic metal complex catalyst such as bis(triphenylphosphine)dichloronickel or dichloro(2,2'-bipyridine)nickel, $PdCl_2$(2,2'-bipyridine) may be employed, since polymerization proceeds under relatively mild conditions. Nitrogen-containing compounds such as bipyridine, or phosphorus-containing organic compounds such as phosphine may also be co-present as a co-catalyst.

As examples of the organic metal complex, those consisting of the central metal from Groups III–XI, preferably from Groups VI–XI of the Periodic Table, with ligands such as a phosphine; an aromatic amine such as pyridine or bipyridine, a halogen atom, etc. are preferably employed. Preferably, the central metal takes so-called tetra- to hexavalent coordination and more preferably, is a metal from Group X of the Periodic Table. Examples of the phosphine include, but are not limited to, triphenylphosphine and methyldiphenylphosphine.

Polymerization using magnesium as a reducing agent is described in T. Yamamoto et al., Bull. Chem. Soc. Jpn., 1978, 51, 2091, T. Yamamoto, Prog. Polym. Sci., 1992, 17, 1155, and M. Rehahan et al., Polymer, 1989, 30, 1054.

Polymerization using zinc as a reducing agent is described in, e.g., T. Yamamoto et al., Makromol. Chem., 1989, 190, 1649, M. Ueda et al., Macromolecules, 1990, 23, 926, I. Colon et al., J. Polym. Sci., Polym. Chem. Ed., 1990, 28, 367, M. Ueda et al., J. Polym. Sci., Chem. Ed., 1992, 30, 1567, V. Chaturvede et al., and J. Chem. Soc., Chem. Commun., 1992, 1658.

The polymerization is carried out preferably at temperatures from −80° C. to 300° C., more preferably at 0° C. to 150° C. Pressure is applied in the range of 0.1 bar to 2500 bars, preferably 0.5 bar to 10 bars. The polymerization can be carried out continuously or batch-wise, in one step or in a multi-step, in a solution or a suspension, in a gaseous phase or in a supercritical medium.

As a solvent, an aliphatic or aromatic solvent can be used; preferably, a polar solvent is employed. Examples of the solvent are an ethereal solvent such as tetrahydrofuran or diethyl ether, a halogenated hydrocarbon such as methylene chloride, a halogenated aromatic hydrocarbon such as o-dichlorobenzene, an amide such as N,N-dimethylformamide, and a sulfoxide such as dimethylsulfoxide.

In a still further aspect of the present invention, there is provided a process for producing a teraryl represented by formula (IIIa) or (IVa) described above. This reaction is shown by the following equation:

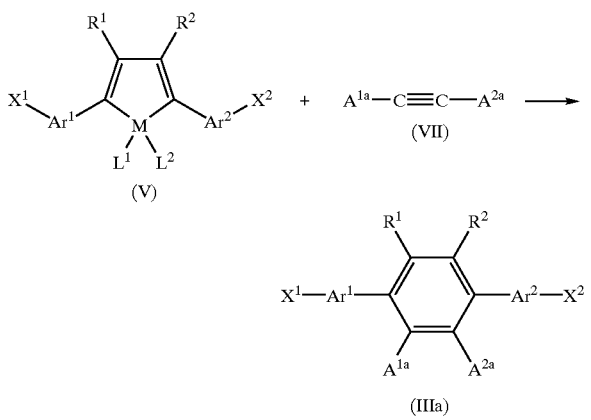

(wherein $Ar^1$, $Ar^2$, $R^1$, $R^2$, $A^{12}$, $A^{22}$, $X^1$ and $X^2$ have the same significance as defined above);

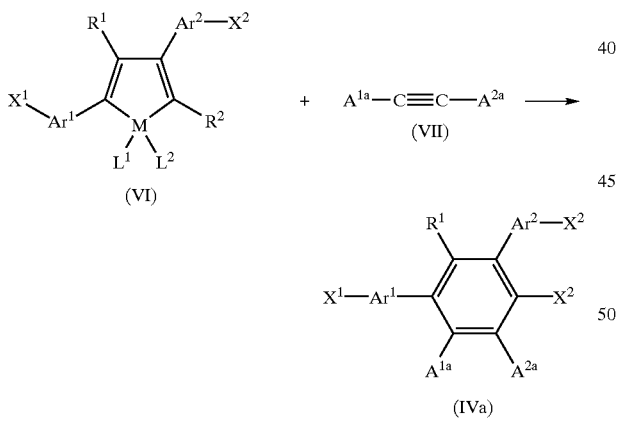

(wherein $Ar^1$, $Ar^2$, $R^1$, $R^2$, $A^{1a}$, $A^{2a}$, $X^1$ and $X^2$ have the same significance as defined above);

The reaction is carried out preferably in the presence of a catalyst. As the catalyst there can be used metal compounds from Groups IV–XV of the Periodic Table, particularly metal compounds from Groups VIII–XV of the Periodic Table. For example, metal salts such as CuX, $NiX_2$ or $BiX_3$ (wherein X is a halogen atom such as chlorine or bromine atom) are employed. Alternatively, the organometallic complexes, especially a nickel complex, which are herein exemplified in the description on the polymerization may be employed.

The formation of a benzene ring by reacting a metallacyclopentadiene such as zirconacyclopentadiene with an acetylene derivative in the presence of CuCl is described in T. Takahashi et al., J. Am. Chem. Soc., 1998, 120, 1672–1680.

Where at least one of $A^{1a}$ and $A^{2a}$ is an electron-donating group such as an alkyloxycarbonyl group, an aryloxycarbonyl group, nitrile group, etc., a copper salt such as copper chloride is preferably used. On the other hand, where $A^{1a}$ and $A^{2a}$ are an alkyl group, an aryl group, an alkoxy group, an aryloxy group, etc., a nickel complex is preferably used.

When of $A^{1a}$ and $A^{2a}$ is cyano group or an alkoxycarbonyl group, this substituent can be converted into carbamoyl group (—C(=O)$NH_2$), a haloformyl group (—C(=O)—X, wherein X is a halogen atom) or formyl group (—C(=O)—H).

The reaction is carried out preferably at temperatures from −80° C. to 300° C., more preferably at −20° C. to 50° C. Pressure is applied in the range of 0.1 bar to 2500 bars, preferably 0.5 bar to 10 bars. The reaction is preferably carried out in situ without separating the metallacyclopentadiene shown by formula (V) or (VI) described above.

In a still further aspect of the present invention, the metallacyclopentadiene shown by formula (V) or (VI) described above is provided. The metallacyclopentadiene can be synthesized from a metallocene according to the following equation:

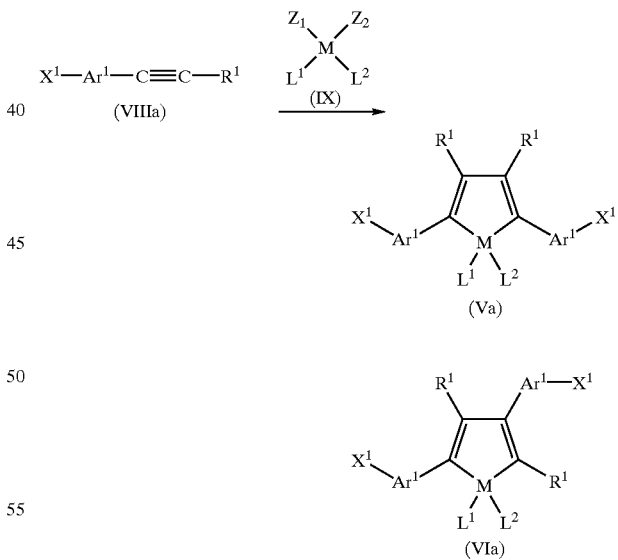

(wherein $Ar^1$, $R^1$, $A^1$, $X^1$, $L^1$ and $L^2$ have the same significance as defined above; B is a crosslinking group; and $Z^1$ and $Z^2$, which may be the same or different, each represents independently a ligand that can be split off);

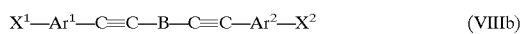

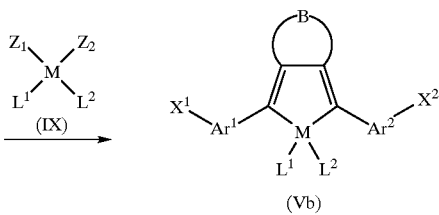

(wherein $Ar^1$, $Ar^2$, $X^1$, $X^2$, $L^1$ and $L^2$ have the same significance as defined above; B is a crosslinking group; and $Z^1$ and $Z^2$, which may be the same or different, each represents independently a ligand that can be split off);

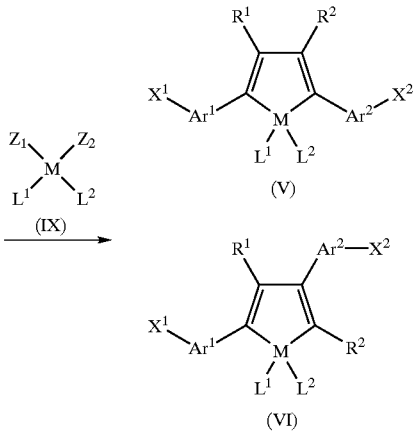

(wherein $Ar^1$, $Ar^2$, $R^1$, $R^2$, $X^1$, $X^2$, $L^1$ and $L^2$ have the same significance as defined above; and $Z^1$ and $Z^2$, which may be the same or different, each represents a ligand that can be split off).

B is a crosslinking group and hydrocarbon group, which may be intervened by, e.g., an oxygen atom, especially an alkylene group which may be intervened by an oxygen atom.

There is no restriction on $Z^1$ and $Z^2$, so long as they can be coordinated with M. Examples of $Z^1$ and $Z^2$ include a halogen atom, an olefin such as ethylene, an alkyl group, and the like.

The reaction described above is carried out preferably at −120° C. to 50° C., more preferably at −120° C. to 0° C., in the presence of a strong base such as an alkyl lithium. The formation of metallacyclopentadienes is described in, e.g., J. Am. Chem. Soc., 1994, 116, 1880–1889.

As M, metal complexes containing metals from Group IV or the lanthanide metal series of the Periodic Table are preferably employed. Metal complexes containing a non-localized cyclic $\eta^5$-coordination type ligand are also preferred.

$L^1$ and $L^2$ are preferably a non-localized cyclic $\eta^5$-coordination type ligand. Examples of the non-localized cyclic $\eta^5$-coordination type ligand are unsubstituted cyclopentadienyl group and a substituted cyclopentadienyl group. Examples of the substituted cyclopentadienyl group include methylcyclopentadienyl, ethylcyclopentadienyl, isopropylcyclopentadienyl, t-butylcyclopentadienyl, dimethylcyclopentadienyl, diethylcyclopentadienyl, diisopropylcyclopentadienyl, di-t-butylcyclopentadienyl, tetramethylcyclopentadienyl, indenyl, 2-methylindenyl, 2-methyl-4-phenylindenyl, tetrahydroindenyl, benzindenyl, fluorenyl, benzofluorenyl, tetrahydrofluorenyl and octahydrofluorenyl groups.

In the non-localized cyclic $\eta^5$-coordination type ligand, one or more atoms of the non-localized cyclic $\eta^5$-coordination type may be substituted for the hetero atom. The ligand may contain, in addition to hydrogen, one or more hetero atoms such as the elements from Group XIV and/or Groups XV, XVI and XVII, of the Periodic Table.

The non-localized cyclic $\eta^5$-coordination type ligand, e.g., the cyclopentadienyl group may be crosslinked with the central metal by one or more crosslinking ligands that may be cyclic. Examples of the crosslinking ligands are $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, $o$-$C_6H_4$ or $2,2'$-$(C_6H_4))_2$.

Two or more non-localized cyclic $\eta^5$-coordination type ligands, e.g., the cyclopentadienyl groups may be crosslinked with each other by one or more crosslinking ligands that may be cyclic. Examples of the crosslinking ligands are $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(C_6H_5)_2Sn$, $(CH_2)_4Si$, $CH_2Si(CH_3)_2$, $o$-$C_6H_4$ or $2,2'$-$(C_6H_4)_2$.

The metallacyclopentadienes of the present invention also embrace compounds containing two or more metallacyclopentadiene moieties. Such compounds are known as multinuclear metallocenes. The multinuclear metallocenes described above may have any substitution mode or any crosslinking mode. The independent metallocene moieties in the multinuclear metallocene may be the same or different. Examples of the multinuclear metallocenes are described in, e.g., EP-A-632063, Japanese Patent Unexamined Publication (Laid-open) Nos. 4-80214 and 4-85310 and EP-A-654476.

The metallacyclopentadienes of the present invention can be synthesized using, e.g., the metallocenes below.

In the case of dichloro-compounds such as bis(indenyl)dichlorozirconium;

bis(fluorenyl)dichorozirconium;

(indenyl)(fluorenyl)dichlorozirconium;

bis(cyclopentadienyl)dichlorotitanium;

(dimethylsilanediyl)bis(indenyl)dichlorozirconium;

(dimethylsilanediyl)bis(tetrahydroindenyl) dichlorozirconium; (dimethylsilanediyl)(indenyl) dichlorozirconium;

(dimethylsilanediyl)bis(2-methylindenyl) dichlorozirconium;

(dimethylsilanediyl)bis(2-ethylindenyl) dichlorozirconium;

(dimethylsilanediyl)bis(2-methyl-4,5-benzindenyl) dichlorozirconium;

(dimethylsilanediyl)bis(2-ethyl-4,5-benzindenyl) dichlorozirconium;

(dimethylsilanediyl)bis(2-methyl-4-phenylindenyl) dichlorozirconium;

(dimethylsilanediyl)bis(2-ethyl-4-phenylindenyl) dichlorozirconium;

(dimethylsilanediyl)bis(2-methyl-4,6-diisopropylindenyl)dichlorozirconium; etc., the metallacyclopentadienes are formed either after reduction of these compounds with a strong base, e.g.,an alkali metal such as sodium, an alkaline earth metal such as magnesium, or after their conversion into the corresponding dialkyl compounds. Examples of the metallocens are:

bis(cyclopentadienyl)dibutylzirconium;
bis(indenyl)dibutylzirconium;
bis(fluorenyl)dibutylzirconium;
(indenyl)(fluorenyl)dibutylzirconium;
(3-methyl-5-naphthylindenyl)(2,7-di-tert-butylfluorenyl) dibutylzirconium;
(3-methyl-5-naphthylindenyl)(3,4,7-trimethoxyfluorenyl) dibutylzirconium;
(pentamethylcyclopentadienyl)(tetrahydroindenyl) dibutylzirconium;
(cyclopentadienyl)(1-octene-8-ylcyclopentadienyl) dibutyzirconium;
(indenyl)(1-butene-4-ylcyclopentadienyl) dibutylzirconium;
[1,3-bis(trimethylsilyl)cyclopentadienyl](3,4-benzofluorenyl)dibutylzirconium;
bis(cyclopentadienyl)dibutyltitanium;
dimethylsilanediylbis(indenyl)dibutylzirconium;
dimethylsilanediylbis(tetrahydroindenyl) dibutylzirconium;
dimethylsilanediyl(cyclopentadienyl)(indenyl) dibutylzirconium;
dimethylsilanediylbis(2-methylindenyl) dibutylzirconium;
dimethylsilanediylbis(2-ethylindenyl)dibutylzirconium;
dimethylsilanediylbis(2-methyl-4,5-benzindenyl) dibutylzirconium;
dimethylsilanediylbis(2-ethyl-4,5-benzindenyl) dibutylzirconium;
dimethylsilanediylbis(4,5-dihydro-8-methyl-7H-cyclopent[e]acenaphthylene-7-ylidene) dibutylzirconium;
dimethylsilanediyl(2-methyl-4,5-benzindenyl)(2-methyl-4-phenylindenyl)dibutylzirconium;
dimethylsilanediyl(2-ethyl-4,5-benzindenyl)(2-methyl-4-phenylindenyl)dibutylzirconium;
dimethylsilanediyl(2-methyl-4,5-benzindenyl)(2-ethyl-4-phenylindenyl)dibutylzirconium;
dimethylsilanediyl(2-ethylindenyl)(2-ethyl-4-phenylnaphthyl)dibutylzirconium;
dimethylsilanediyl(2-methylindenyl)(4-phenylindenyl) dibutylzirconium;
dimethylsilanediylbis(2-methyl-4-phenylindenyl) dibutylzirconium;
dimethylsilanediylbis(2-ethyl-4-phenylindenyl) dibutylzirconium;
dimethylsilanediylbis(2-methyl-4,6-diisopropylindenyl) dibutylzirconium;
dimethylsilanediylbis(2-ethyl-4,6-diisopropylindenyl) dibutylzirconium;
dimethylsilanediylbis(2-methyl-4-naphthylindenyl) dibutyzirconium;
dimethylsilanediylbis(2-ethyl-4-naphthylindenyl) dibutylzirconium;
methylphenylsilanediylbis(indenyl)dibutylzirconium;
methylphenylsilanediyl(cyclopentadienyl)(indenyl) dibutylzirconium;
methylphenylsilanediylbis(tetrahydroindenyl) dibutylzirconium;
methylphenylsilanediylbis(2-methylindenyl) dibutylzirconium;
methylphenylsilanediylbis(2-ethylindenyl) dibutylzirconium;
methylphenylsilanediylbis(2-methyl-4,5-benzindenyl) dibutylzirconium;
methylphenylsilanediylbis(2-ethyl-4,5-benzindenyl) dibutylzirconium;
methylphenylsilanediylbis(4,5-dihydro-8-methyl-7H-cyclopent[e]acenaphthylene-7-ylidene) dibutylzirconium;
methylphenylsilanediyl(2-methyl-4,5-benzindenyl)(2-methyl-4-phenylindenyl)dibutylzirconium;
methylphenylsilanediyl(2-ethylindenyl)(2-methyl-4-phenylindenyl)dibutylzirconium;
methylphenylsilanediyl(2-methyl-4,5-benzindenyl)(2-ethyl1-4-phenylindenyl)dibutylzirconium;
methylphenylsilanediyl(2-ethyl-4,5-benzindenyl)(2-ethyl-indenyl)dibutylzirconium;
methylphenylsilanediyl(2-methylindenyl)(4-phenylindenyl)dibutylzirconium;
methylphenylsilanediylbis(2-methyl-4-phenylindenyl) dibutylzirconium;
methylphenylsilanediylbisdibutylzirconium;
methylphenylsilanediylbis(2-methyl-4,6-diisopropylindenyl)dibutylzirconium;
methylphenylsilanediylbis(2-ethyl-4,6-diisopropylindenyl)dibutylzirconium;
methylphenylsilanediylbis(4-naphthylindenyl) dibutylzirconium;
methylphenylsilanediylbis(2-ethyl-4-naphthylindenyl) dibutylzirconium;
diphenylsilanediylbis(indenyl)dibutylzirconium;
diphenylsilanediylbis(2-methylindenyl)dibutylzirconium;
diphenylsilanediylbis(2-ethylindenyl)dibutylzirconium;
diphenylsilanediyl(cyclopentadienyl)(indenyl) dibutylzirconium;
diphenylsilanediylbis(2-methyl-4,5-benzindenyl) dibutylzirconium;
diphenylsilanediylbis(2-ethyl-4,5-benzindenyl) dibutylzirconium;
diphenylsilanediyl(2-methyl-4,5-benzindenyl)(2-methyl-4-phenylindenyl)dibutylzirconium;
diphenylsilanediyl(2-ethyl-4,5-benzindenyl)(2-methyl-4-phenylindenyl)dibutylzirconium;
diphenylsilanediyl(2-methyl-4,5-benzindenyl)(2-ethyl-4-phenylindenyl)dibutylzirconium;
diphenylsilanediyl(2-ethyl-4,5-benzindenyl)(2-ethyl-4-naphthylindenyl)dibutylzirconium;
diphenylsilanediyl(2-methylindenyl)(4-phenylindenyl) dibutylzirconium;
diphenylsilanediylbis(2-methyl-4-phenylindenyl) dibutylzirconium;
diphenylsilanediylbis(2-ethyl-4-phenylindenyl) dibutylzirconium;
diphenylsilanediylbis(2-methyl-4,6-diisopropylindenyl) dibutylzirconium;
diphenylsilanediylbis(2-ethyl-4,6-diisopropylindenyl) dibutylzirconium;
diphenylsilanediylbis(2-methyl-4-naphthylindenyl) dibutyzirconium;
diphenylsilanediylbis(2-ethyl-4-naphthylindenyl) dibutylzirconium;

1-silacyclopentane-1,1-bis(indenyl)dibutylzirconium;
1-silacyclopentane-1,1-bis(2-methylindenyl)dibutylzirconium;
1-silacyclopentane-1,1-bis(2-ethylindenyl)dibutylzirconium;
1-silacyclopentane-1,1-bis(2-methyl-4,5-benzindenyl)dibutylzirconium;
1-silacyclopentane-1,1-bis(2-ethyl-4,5-benzindenyl)dibutylzirconium;
1-silacyclopentane-1-(2-methyl-4,5-benzindenyl)-1-(2-methyl-4-phenylindenyl)dibutylzirconium;
1-silacyclopentane-1-(2-ethyl-4,5-benzindenyl)-1-(2-methyl-4-phenylindenyl)dibutylzirconium;
1-silacyclopentane-1-(2-methyl-4,5-benzindenyl)-1-(2-ethyl-4-phenylindenyl)dibutylzirconium;
1-silacyclopentane-1-(2-ethyl-4,5-benzindenyl)-1-(2-ethyl-4-naphthylindenyl)dibutylzirconium;
1-silacyclopentane-1-(2-methylindenyl)-1-(4-phenylindenyl)dibutylzirconium;
1-silacyclopentane-1,1-bis(2-methyl-4-phenylindenyl)dibutylzirconium;
1-silacyclopentane-1,1-bis(2-ethyl-4-phenylindenyl)dibutylzirconium;
1-silacyclopentane-1,1-bis(2-methyl-4,6-diisopropylindenyl)dibutylzirconium;
1-silacyclopentane-1,1-bis(2-ethyl-4,6-diisopropylindenyl)dibutylzirconium;
1-silacyclopentane-1,1-bis(2-methyl-4-naphthylindenyl)dibutylzirconium;
1-silacyclopentane-1,1-bis(2-ethyl-4-naphthylindenyl)dibutylzirconium;
bis(cyclopentadienyl)dibutyltitanium;
ethylene-1,2-bis(indenyl)dibutylzirconium;
ethylene-1,2-bis(tetrahydroindenyl)dibutylzirconium;
ethylene-1-(cyclopentadienyl)-2-(1-indenyl)dibutylzirconium;
ethylene-1-(cyclopentadienyl)-2-(2-indenyl)dibutylzirconium;
ethylene-1-(cyclopentadienyl)-2-(2-methyl-1-indenyl)dibutylzirconium;
ethylene-1,2-bis(2-methylindenyl)dibutylzirconium;
ethylene-1,2-bis(2-ethylindenyl)dibutylzirconium;
ethylene-1,2-bis(2-methyl-4,5-benzindenyl)dibutylzirconium;
ethylene-1,2-bis(2-ethyl-4,5-benzindenyl)dibutylzirconium;
ethylene-1,2-bis(4,5-dihydro-8-methyl-7H-cyclopent[e]acenaphthylene-7-ylidene)dibutylzirconium;
ethylene-1-(2-methyl-4,5-benzindenyl)-2-(2-methyl-4-phenylindenyl)dibutylzirconium;
ethylene-1-(2-ethyl-4,5-benzindenyl)-2-(2-methyl-4-phenylindenyl)dibutylzirconium;
ethylene-1-(2-methyl-4,5-benzindenyl)-2-(2-ethyl-4-phenylindenyl)dibutylzirconium;
ethylene-1-(2-ethyl-4,5-benzindenyl)-2-(2-ethyl-4-naphthylindenyl)dibutylzirconium;
ethylene-1-(2-methylindenyl)-2-(4-phenylindenyl)dibutylzirconium;
ethylene-1,2-bis(2-methyl-4-phenylindenyl)dibutylzirconium;
ethylene-1,2-bis(2-ethyl-4-phenylindenyl)dibutylzirconium;
ethylene-1,2-bis(2-methyl-4,6-diisopropylindenyl)dibutylzirconium;
ethylene-1,2-bis(2-ethyl-4,6-diisopropylindenyl)dibutylzirconium;
ethylene-1,2-bis(2-methyl-4-naphthylindenyl)dibutylzirconium;
ethylene-1,2-bis(2-ethyl-4-naphthylindenyl)dibutylzirconium;
propylene-2,2-bis(indenyl)dibutylzirconium;
propylene-2-cyclopentadienyl-2-(1-indenyl)dibutylzirconium;
propylene-2-cyclopentadienyl-2-(4-phenyl-1-indenyl)dibutylzirconium;
propylene-2-cyclopentadienyl-2-(9-fluorenyl)dibutylzirconium;
propylene-2-cyclopentadienyl-2-(2,7-dimethoxy-9-fluorenyl)dibutylzirconium;
propylene-2-cyclopentadienyl-2-(2,7-di-tert-butyl-9-fluorenyl)dibutylzirconium;
propylene-2-cyclopentadienyl-2-(2,7-dibromo-9-fluorenyl)dibutylzirconium;
propylene-2-cyclopentadienyl-2-(2,7-diphenyl-9-fluoreny]dibutylzirconium;
propylene-2-cyclopentadienyl-2-(2,7-dimethyl-9-fluorenyl)dibutylzirconium;
propylene-2-(3-methylcyclopentadienyl)-2-(2,7-dibutyl-9-fluorenyl)dibutylzirconium;
propylene-2-(3-tert-butylcyclopentadienyl)-2-(2,7-dibutyl-9-fluorenyl)dibutylzirconium;
propylene-2-(3-trimethylsilylcyclopentadienyl)-2-(3,6-di-tert-butyl-9-fluorenyl)dibutylzirconium;
propylene-2-cyclopentadienyl-2-[2,7-bis(3-butene-1-yl)-9-fluorenyl]dibutylzirconium;
propylene-2-cyclopentadienyl-2-(3-tert-butyl-9-fluorenyl)dibutylzirconium;
propylene-2,2-bis(tetrahydroindenyl)dibutylzirconium;
propylene-2,2-bis(2-methylindenyl)dibutylzirconium;
propylene-2,2-bis(2-ethylindenyl)dibutylzirconium;
propylene-2,2-bis(2-methyl-4,5-benzindenyl)dibutylzirconium;
propylene-2,2-bis(2-ethyl-4,5-benzindenyl)dibutylzirconium;
propylene-2,2-bis(4,5-dihydro-8-methyl-7H-cyclopent[e]acenaphthylene-7-ylidene)dibutylzirconium;
propylene-2-(2-methyl-4,5-benzindenyl)-2-(2-methyl-4-phenylindenyl)dibutylzirconium;
propylene-2-(2-ethyl-4,5-benzindenyl)-2-(2-methyl-4-phenylindenyl)dibutylzirconium;
propylene-2-(2-methyl-4,5-benzindenyl)-2-(2-ethyl-4-phenylindenyl)dibutylzirconium;
propylene-2-(2-ethyl-4,5-benzindenyl)-2-(2-ethyl-4-naphthylindenyl)dibutylzirconium;
propylene-2-(2-methylindenyl)-2-(4-phenylindenyl)dibutyzirconium;
propylene-2,2-bis(2-methyl-4-phenylindenyl)dibutylzirconium;
propylene-2,2-bis(2-ethyl-4-phenylindenyl)dibutylzirconpropylene-2,2-bis(2-methyl-4,6-diisopropylindenyl)dibutylzirconium;
propylene-2,2-bis(2-ethyl-4,6-diisopropylindenyl)dibutylzirconium;

propylene-2,2-bis(2-methyl-4-naphthylindenyl)dibutylzirconium;
propylene-2,2-bis(2-ethyl-4-naphthylindenyl)dibutylzirconium;
1,6-bis[methylsilylbis(2-methyl-4-phenylindenyl)dibutylzirconium]hexane;
1,6-bis[methylsilylbis(2-methyl-4,5-benzindenyl)dibutylzirconium]hexane;
1,6-bis[methylsilylbis(2-ethyl-4-phenylindenyl)dibutylzirconium]hexane;
1,6-bis[methylsilylbis(2-methyl-4-naphthylindenyl)dibutylzirconium]hexane;
1,6-bis[methylsilylbis(2-methyl-4,6-diisopropylindenyl)dibutylzirconium]hexane;
1,6-bis[methylsilyl(2-methyl-4-phenylindenyl)(4,5-benzindenyl)dibutylzirconium]hexane;
1-[methylsilylbis(tetrahydroindenyl)dibutylzirconium]-6-[ethylstannyl(cyclopentadienyl)(fluorenyl)dibutylzirconium]hexane;
1,6-disila-1,1,6,6-tetramethyl-1,6-bis[methylsilylbis(2-methyl-4-phenylindenyl)dibutylzirconium]hexane;
1,4-disila-1,4-bis[methylsilylbis(2-methyl-4-phenylindenyl)dibutylzirconium]cyclohexane;
[1,4-bis(1-indenyl)-1,1,4,4-tetramethyl-1,4-disilabutane]bis(pentamethylcyclopentadienyldibutylzirconium);
[1,4-bis(9-fluorenyl)-1,1,4,4-tetramethyl-1,4-disilabutane]bis(cyclopentadienyldibutylzirconium);
[1,4-bis(1-indenyl)-1,1,4,4-tetramethyl-1,4-disilabutane]bis(cyclopentadienyldibutylzirconium);
[1-(1-indenyl)-6-(2-phenyl-1-indenyl)-1,1,6,6-tetraethyl-1,6-disila-4-oxahexane]bis(tert-butylcyclopentadienyldibutylzirconium);
[1,10-bis(2,3-dimethyl-1-indenyl)-1,1,10,10-tetramethyl-1,10-digermadecane]bis(2-methyl-4-phenylindenyldibutylzirconium);
(1-methyl-3-tert-butylcyclopentadienyl)(1-phenyl-4-methoxy-7-chlorofluorenyl)dibutylzirconium;
(4,7-dichloroindenyl)(3,6-dimesitylfluorenyl)dibutylzirconium;
bis(2,7-di-tert-butyl-9-cyclohexylfluorenyl)dibutylzirconium;
(2,7-dimethylfluorenyl)[2,7-bis(1-naphthyl)fluorenyl]dibutylzirconium;
dimethylsilylbis(fluorenyl)dibutylzirconium;
dibutylstannylbis(2-methylfluorenyl)dibutylzirconium;
1,1,2,2-tetraethyldisilanediyl(2-methylindenyl)(4-phenylfluorenyl)dibutylzirconium;
propylene-1-(2-indenyl)-2-(9-fluorenyl)dibutylzirconium;
1,1-dimethyl-1-silaethylenebis(fluorenyl)dibutylzirconium;
[4-(cyclopentadienyl)4,7,7-trimethyl(tetrahydroindenyl)dibutylzirconium;
[4-(cyclopentadienyl)-4,7-dimethyl-7-phenyl(5,6-dimethyl]tetrahydroindenyl]dibutylzirconium;
[4-(cyclopentadienyl)-4,7-dimethyl-7-(1-naphthyl)(7-phenyltetrahydroindenyl)]dibutylzirconium;
[4-(cyclopentadienyl)-4,7-dimethyl-7-butyl(6,6-diethyltetrahydroindenyl)]dibutylzirconium;
[4-(3-tert-butylcyclopentadienyl)-4,7,7-trimethyl(tetrahydroindenyl)]dibutylzirconium;
[4-(1-indenyl)-4,7,7-trimethyl(tetrahydroindenyl)]dibutylzirconium;
bis(cyclopentadienyl)dibutylhafnium;
bis(indenyl)dibutylvanadium;
bis(fluorenyl)dibutylscandium;
(indenyl)(fluorenyl)dibutylniobium;
(2-methyl-7-naphthylindenyl)(2,6-di-tert-butylfluorenyl)dibutyltitanium;
(pentamethylcyclopentadienyl)(tetrahydroindenyl)butylhafnium bromide;
(cyclopentadienyl)(1-octene-8-ylcyclopentadienyl)dibutylhafnium;
(indenyl)(2-butene-4-ylcyclopentadienyl)dibutyltitanium;
[1,3-bis(trimethylsilyl)cyclopentadienyl](3,4-penzofluorenyl)dibutylniobium;
bis(cyclopentadienyl)dibutyltitanium;
dimethylsilanediylbis(indenyl)dibutyltitanium;
dimethylsilanediylbis(tetrahydroindenyl)dibutylhafnium;
dimethylsilanediyl(cyclopentadienyl)(indenyl)dibutyltitanium;
dimethylsilanediylbis(2-methylindenyl)dibutylhafnium;
dimethylsilanediylbis(2-ethylindenyl)methylscandium;
dimethylsilanediylbis(2-butyl-4,5-benzindenyl)dibutylniobium;
dimethylsilanediylbis(2-ethyl-4,5-benzindenyl)dibutyltitanium;
dimethylsilanediylbis(4,5-dihydro-8-methyl-7H-cyclopent[e]acenaphthylene-7-ylidene)dibutyltitanium;
dimethylsilanediyl(2-methyl-4,5-benzindenyl)(2-methyl-4-phenylindenyl)dibutyltitanium;
dimethylsilanediyl(2-ethyl-4,5-benzindenyl)(2-methyl-4-phenylindenyl)dibutylhafnium;
dimethylsilanediyl(2-ethyl-4,5-benzindenyl)(2-ethyl-4-phenylindenyl)methylscandium;
dimethylsilanediyl(2-ethyl-4,5-benzindenyl)(2-ethyl-4-naphthylindenyl)dibutyltitanium;
dimethylsilanediyl(2-methylindenyl)(4-phenylindenyl)dibutylhafnium;
dimethylsilanediylbis(2-methyl-4-phenylindenyl)dibutylniobium;
dimethylsilanediylbis(2-ethyl-4-phenylindenyl)dibutylvanadium;
dimethylsilanediylbis(2-methyl-4,6-diisopropylindenyl)dibutylhafnium;
dimethylsilanediylbis(2-methyl-4,6-diisopropylindenyl)dibutylvanadium;
dimethylsilanediylbis(2-methyl-4-naphthylindenyl)butylhafnium bromide;
dimethylsilanediylbis(2-ethyl-4-naphthylindenyl)dibutyltitanium;
methylphenylsilanediylbis(indenyl)dibutyltitanium;
methylphenylsilanediyl(cyclopentadienyl)(indenyl)hafnium;
methylphenylsilanediylbis(tetrahydroindenyl)dibutylhafnium;
methylphenylsilanediylbis(2-methylindenyl)dibutyltitanium;
methylphenylsilanediylbis(2-ethylindenyl)dibutylhafnium;
methylphenylsilanediylbis(2-methyl-4,5-benzindenyl)dibutylhafnium;

methylphenylsilanediylbis(2-ethyl-4,5-benzindenyl) dibutylvanadium;
methylphenylsilanediylbis(4,5-dihydro-8-methyl-7H-cyclopent[e]acenaphthylene-7-ylidene) dibutyltitanium;
methylphenylsilanediylbis(2-methyl-4,5-benzindenyl)(2-methyl-4-phenylindenyl)butyltitanium bromide;
methylphenylsilanediylbis(2-ethyl-4,5-benzindenyl)(2-methyl-4-phenylindenyl)dibutyltitanium;
methylphenylsilanediylbis(2-methyl-4,5-benzindenyl)(2-ethyl-4-phenylindenyl)dibutylhafnium;
methylphenylsilanediylbis(2-ethyl-4,5-benzindenyl)(2-ethyl-4-phenylindenyl)dibutylhafnium;
methylphenylsilanediyl(2-methylindenyl)(4-phenylindenyl)dibutyltitanium;
methylphenylsilanediylbis(2-methyl-4-phenylindenyl) dibutylhafnium;
methylphenylsilanediylbis(2-ethyl-4-phenylindenyl) dibutylvanadium;
methylphenylsilanediylbis(2-methyl-4,6-diisopropylindenyl)dibutyltitanium;
methylphenylsilanediylbis(2-ethyl-4,6-diisopropylindenyl)dibutylhafnium;
methylphenylsilanediylbis(2-methyl-4-naphthylindenyl) dibutylhafnium;
methylphenylsilanediylbis(2-ethyl-4-naphthylindenyl) dibutyltitanium;
diphenylsilanediylbis(indenyl)dibutyltitanium;
diphenylsilanediylbis(2-methylindenyl)dibutylhafnium;
diphenylsilanediylbis(2-ethylindenyl)dibutyltitanium;
diphenylsilanediylbis(cyclopentadienyl)(indenyl) dibutylhafnium;
diphenylsilanediylbis(2-methyl-4,5-benzindenyl) dibutyltitanium;
diphenylsilanediylbis(2-ethyl-4,5-benzindenyl) dibutylhafnium;
diphenylsilanediyl(2-methyl-4,5-benzindenyl)(2-methyl-4,5-phenylindenyl)dibutylhafnium;
diphenylsilanediyl(2-ethyl-4,5-benzindenyl)(2-methyl-4,5-phenylindenyl)dibutyltitanium;
diphenylsilanediyl(2-methyl-4,5-benzindenyl)(2-ethyl-4,5-phenylindenyl)dibutylhafnium;
diphenylsilanediyl(2-ethyl-4,5-benzindenyl)(2-ethyl-4,5-phenylindenyl)dibutyltitanium;
diphenylsilanediyl(2-methylindenyl)(4-phenylindenyl) dibutyltitanium;
diphenylsilanediylbis(2-methyl-4-phenylindenyl) dibutyltitanium;
diphenylsilanediylbis(2-ethyl-4-phenylindenyl) dibutylhafnium;
diphenylsilanediylbis(2-methyl-4,6-diisopropylindenyl) dibutylhafnium;
diphenylsilanediylbis(2-ethyl-4,6-diisopropylindenyl) dibutylhafnium;
diphenylsilanediylbis(2-methyl-4-naphthylindenyl) dibutylhafnium;
diphenylsilanediylbis(2-ethyl-4-naphthylindenyl) dibutyltitanium;
1-silacyclopentane-1,1-bis(indenyl)dibutylhafnium;
1-silacyclopentane-1,1-bis(2-methylindenyl) dibutylhafnium;
1-silacyclopentane-1,1-bis(2-ethylindenyl) dibutylhafnium;
1-silacyclopentane-1,1-bis(2-methyl-4,5-benzindenyl) dibutyltitanium;
1-silacyclopentane-1,1-bis(2-ethyl-4,5-benzindenyl) dibutylhafnium;
1-silacyclopentane-1-(2-methyl-4,5-benzindenyl)-1-(2-methyl-4-phenylindenyl)methylscandium;
1-silacyclopentane-1-(2-ethyl-4,5-benzindenyl)-1-(2-methyl-4-phenylindenyl)dibutylhafnium;
1-silacyclopentane-1-(2-methyl-4,5-benzindenyl)-1-(2-ethyl-4-phenylindenyl)dibutyltitanium;
1-silacyclopentane-1-(2-ethyl-4,5-benzindenyl)-1-(2-ethyl-4-phenylindenyl)dibutylhafnium;
1-silacyclopentane-1-(2-methylindenyl)-1-(4-phenylindenyl)dibutylhafnium;
1-silacyclopentane-1,1-bis(2-methyl-4-phenylindenyl) dibutylhafnium;
1-silacyclopentane-1,1-bis(2-ethyl-4-phenylindenyl) dibutyltitanium bromide;
1-silacyclopentane-1,1-bis(2-methyl-4,6-diisopropylindenyl)dibutyltitanium;
1-silacyclopentane-1,1-bis(2-ethyl-4,6-diisopropylindenyl)dibutyltitanium;
1-silacyclopentane-1,1-bis(2-methyl-4-naphthylindenyl) methylscandium;
1-silacyclopentane-1,1-bis(2-ethyl-4-naphthylindenyl) dibutylhafnium;
bis(cyclopentadienyl)dibutyltitanium;
ethylene-1,2-bis(indenyl)methylscandium;
ethylene-1,2-bis(tetrahydroindenyl)dibutyltitanium;
ethylene-1-(cyclopentadienyl)-2-(1-indenyl) dibutylhafnium;
ethylene-1-(cyclopentadienyl)-2-(2-indenyl) butyltitanium bromide;
ethylene-1-(cyclopentadienyl)-2-(2-methyl-1-indenyl) dibutylhafnium;
ethylene-1,2-bis(2-methylindenyl)dibutylhafnium;
ethylene-1,2-bis(2-ethylindenyl)dibutylhafnium;
ethylene-1,2-bis(2-methyl-4,5-benzindenyl) dibutylhafnium;
ethylene-1,2-bis(2-ethyl-4,5-benzindenyl) dibutyltitanium;
ethylene-1,2-bis(4,5-dihydro-8-methyl-7H-cyclopent[e] acenaphthylene-7-ylidene)dibutyltitanium;
ethylene-1-(2-methyl-4,5-benzindenyl)-2-(2-methyl-4-phenylindenyl)dibutyltitanium;
ethylene-1-(2-ethyl-4,5-benzindenyl)-2-(2-methyl-4-phenylindenyl)dibutyltitanium;
ethylene-1-(2-methyl-4,5-benzindenyl)-2-(2-ethyl-4-phenylindenyl)methylscandium;
ethylene-1-(2-ethyl-4,5-benzindenyl)-2-(2-ethyl-4-naphthylindenyl)dibutylhafnium;
ethylene-1-(2-methylindenyl)-2-(4-phenylindenyl) dibutyltitanium;
ethylene-1,2-bis(2-methyl-4-phenylindenyl) dibutylhafnium;
ethylene-1,2-bis(2-ethyl-4-phenylindenyl) dibutylhafnium;
ethylene-1,2-bis(2-methyl-4,6-diisopropylindenyl) dibutylhafnium;

ethylene-1,2-bis(2-ethyl-4,6-diisopropylindenyl)dibutyltitanium;
ethylene-1,2-bis(2-methyl-4-naphthylindenyl)dibutyltitanium;
ethylene-1,2-bis(2-ethyl-4-naphthylindenyl)dibutylhafnium;
propylene-2,2-bis(indenyl)dibutylhafnium;
propylene-2-cyclopentadienyl-2-(1-indenyl)dibutyltitanium;
propylene-2-cyclopentadienyl-2-(4-phenyl-1-indenyl)dibutyltitanium;
propylene-2-cyclopentadienyl-2-(9-fluorenyl)dibutylhafnium;
propylene-2-cyclopentadienyl-2-(2,7-dimethoxy-9-fluorenyl)dibutylhafnium;
propylene-2-cyclopentadienyl-2-(2,7-di-tert-butyl-9-fluorenyl)dibutylhafnium;
propylene-2-cyclopentadienyl-2-(2,7-dibromo-9-fluorenyl)dibutyltitanium;
propylene-2-cyclopentadienyl-2-(2,7-diphenyl-9-fluorenyl)dibutylhafnium;
propylene-2-cyclopentadienyl-2-(2,7-dimethyl-9-fluorenyl)dibutyltitanium;
propylene-2-(3-methylcyclopentadienyl)-2-(2,7-dibutyl-9-fluorenyl)dibutylhafnium;
propylene-2-(3-tert-butylcyclopentadienyl)-2-(2,7-dibutyl-9-fluorenyl)dibutyltitanium;
propylene-2-(3-trimethylsilylcyclopentadienyl)-2-(3,6-di-tert-butyl-9-fluorenyl)dibutyltitanium;
propylene-2-cyclopentadienyl-2-[2,7-bis(3-butene-1-yl)-9-fluorenyl]dibutylhafnium;
propylene-2-cyclopentadienyl-2-(3-tert-butyl-9-fluoreny-1)dibutyltitanium;
propylene-2,2-bis(tetrahydroindenyl)dibutylhafnium;
propylene-2,2-bis(2-methylindenyl)dibutylhafnium;
propylene-2,2-bis(2-ethylindenyl)dibutyltitanium;
propylene-2,2-bis(2-methyl-4,5-benzindenyl)dibutyltitanium;
propylene-2,2-bis(2-ethyl-4,5-benzindenyl)dibutylhafnium;
propylene-2,2-bis(4,5-dihydro-8-methyl-7H-cyclopent[e]acenaphthylene-7-ylidene)dibutylhafnium;
propylene-2-(2-methyl-4,5-benzindenyl)-2-(2-methyl-4-phenylindenyl)dibutylhafnium;
propylene-2-(2-ethyl-4,5-benzindenyl)-2-(2-methyl-4-phenylindenyl)dibutyltitanium;
propylene-2-(2-methyl-4,5-benzindenyl)-2-(2-ethyl-4-phenylindenyl)dibutylhafnium;
propylene-2-(2-ethyl-4,5-benzindenyl)-2-(2-ethyl-4-naphthylindenyl)dibutyltitanium;
propylene-2-(2-methylindenyl)-2-(4-phenylindenyl)dibutylhafnium;
propylene-2,2-bis(2-methyl-4-phenylindenyl)dibutyltitanium;
propylene-2,2-bis(2-ethyl-4-phenylindenyl)dibutylhafnium;
propylene-2,2-bis(2-methyl-4,6-diisopropylindenyl)dibutyltitanium;
propylene-2,2-bis(2-ethyl-4,6-diisopropylindenyl)dibutylhafnium;
propylene-2,2-bis(2-methyl-4-naphthylindenyl)dibutyltitanium;
propylene-2,2-bis(2-ethyl-4-naphthylindenyl)dibutyltitanium;
1,6-bis[methylsilylbis(2-methyl-4-phenylindenyl)dibutylhafnium]hexane;
1,6-bis[methylsilylbis(2-methyl-4,5-benzindenyl)dibutyltitanium]hexane;
1,6-bis[methylsilylbis(2-ethyl-4-phenylindenyl)dibutylhafnium]hexane;
1,6-bis[methylsilylbis(2-methyl-4-naphthylindenyl)dibutyltitanium]hexane;
1,6-bis[methylsilylbis(2-methyl-4,6-diisopropylindenyl)dibutylhafnium]hexane; 1,6-bis[methylsilyl(2-methyl-4-phenylindenyl)(4,5-benzindenyl)dibutyltitanium]hexane;
1-[methylsilylbis(tetrahydroindenyl)dibutylhafnium]-6-[ethylstannyl(cyclopentadienyl)(fluorenyl)dibutyltitanium]hexane;
1,6-disila-1,1,6,6-tetramethyl-1,6-bis[methylsilylbis(2-methyl-4-phenylindenyl)dibutylhafnium]hexane;
1,4-disila-1,4-bis[methylsilylbis(2-methyl-4-phenylindenyl)dibutylhafnium]cyclohexane;
[1,4-bis(1-indenyl)-1,1,4,4-tetramethyl-1,4-disilabutane]bis(pentamethylcyclopentadienyldibutylhafnium);
[1,4-bis(9-fluorenyl)-1,1,4,4-tetramethyl-1,4-disilabutane]bis(cyclopentadienyldibutylhafnium);
[1,4-bis(1-indenyl)-1,1,4,4-tetramethyl-1,4-disilabutane]bis(cyclopentadienyldibutyltitanium);
[1-(1-indenyl)-6-(2-phenyl-1-indenyl)-1,1,6,6-tetraethyl-1,6-disila-4-oxahexane]bis(tert-butylcyclopentadienyldibutyltitanium);
[1,10-bis(2,3-dimethyl-1-indenyl)-1,1,10,10-tetramethyl-1,10-digermadecane]bis(2-methyl-4-phenylindenyldibutylhafnium);
(1-methyl-3-tert-butylcyclopentadienyl)(1-phenyl-4-methoxy-7-chlorofluorenyl)dibutyltitanium;
(4,7-dichloroindenyl)(3,6-dimesitylfluorenyl)dibutyltitanium;
bis(2,7-di-tert-butyl-9-cyclohexylfluorenyl)dibutylhafnium;
(2,7-dimesitylfluorenyl)[2,7-bis(1-naphthyl)fluorenyl]dibutylhafnium;
dimethylsilylbis(fluorenyl)dibutyltitanium;
dibutylstannylbis(2-methylfluorenyl)dibutylhafnium;
1,1,2,2-tetraethyldisilanediyl(2-methylindenyl)(4-phenylfluorenyl)dibutyltitanium;
propylene-1-(2-indenyl)-2-(9-fluorenyl)dibutylhafnium;
1,1-dimethyl-1-silaethylenebis(fluorenyl)dibutyltitanium;
[4-(cyclopentadienyl)4,7,7-trimethyl(tetrahydroindenyl]dibutyltitanium;
[4-(cyclopentadienyl)4,7-dimethyl-7-phenyl(5,6-dimethyltetrahydroindenyl]dibutylhafnium;
[4-(cyclopentadienyl)-4,7-dimethyl-7-(1-naphthyl)(7-phenyltetrahydroindenyl]dibutyltitanium;
[4-(cyclopentadienyl)-4,7-dimethyl-7-butyl(6.6-diethyltetrahydroindenyl)]dibutylhafnium;
[4-(3-tert-butylcyclopentadienyl)-4,7,7-trimethyl(tetrahydroindenyl)]dibutylhafnium;
[4-(1-indenyl)-4,7,7-trimethyl(tetrahydroindenyl)]dibutyltitanium;
bis(cyclopentadienyl)dibutylhafnium;
bis(cyclopentadienyl)dichlorozirconium;

bis(indenyl)dichlorozirconium;
bis(fluorenyl)dichlorozirconium;
(indenyl)(fluorenyl)dichlorozirconium;
bis(cyclopentadienyl)dichlorotitanium;
(dimethylsilanediyl)bis(indenyl)dichlorozirconium;
(dimethylsilanediyl)bis(tetrahydroindenyl)dichlorozirconium;
(dimethylsilanediyl)(indenyl)dichlorozirconium;
(dimethylsilanediyl)bis(2-methylindenyl)dichlorozirconium;
(dimethylsilanediyl)bis(2-ethylindenyl)dichlorozirconium;
(dimethylsilanediyl)bis(2-methyl-4,5-benzindenyl)dichlorozirconium;
(dimethylsilanediyl)bis(2-ethyl-4,5-benzindenyl)dichlorozirconium;
(dimethylsilanediyl)bis(2-methyl-4-phenylindenyl)dichlorozirconium;
(dimethylsilanediyl)bis(2-ethyl-4-phenylindenyl)dichlorozirconium;
(dimethylsilanediyl)bis(2-methyl-4,6-diisopropylindenyl)dichlorozirconium;
bis(cyclopentadienyl)($\eta_4$-butadiene)zirconium;
bis(methylcyclopentadienyl)($\eta_4$-butadiene)zirconium;
bis(n-butylcyclopentadienyl)($\eta_4$-butadiene)zirconium;
bisindenyl($\eta_4$-butadiene)zirconium;
(tert-butylamido)dimethyl(tetramethyl-$\eta_5$-cyclopentadienyl)silane($\eta_4$-butadiene)zirconium;
bis(2-methylbenzindenyl)($\eta_4$-butadiene)zirconium;
dimethylsilanediylbis(2-methyl-indenyl)($\eta_4$-butadiene)zirconium;
dimethylsilanediylbisindenyl($\eta_4$-butadiene)zirconium;
dimethylsilanediylbis(2-methylindenyl)($\eta_4$-butadiene)zirconium;
dimethylsilanediyl(2-methylbenzindenyl)(2-methyl-indenyl)($\eta_4$-butadiene)zirconium;
dimethylsilanediyl(2-methylbenzindenyl)(2-methyl-4-phenylindenyl)($\eta_4$-butadiene)zirconium;
dimethylsilanediyl(2-methylindenyl)(4-phenylindenyl)($\eta_4$-butadiene)zirconium;
dimethylsilanediylbis(2-methyl-4-phenylindenyl)($\eta_4$-butadiene)zirconium;
dimethylsilanediylbis(2-methyl-4,6-diisopropylindenyl)($\eta_4$-butadiene)zirconium;
dimethylsilanediylbis(2-methyl-4-naphthylindenyl)($\eta_4$-butadiene)zirconium;
isopropylidene(cyclopentadienyl)(fluorenyl)($\eta_4$-butadiene)zirconium;
isopropylidene(cyclopentadienyl)(indenyl)($\eta_4$-butadiene)zirconium;
(4-$\eta_5$-cyclopentadienyl)-4,7,7-trimethyl-($\eta_{5,4,5,6,7}$-tetrahydroindenyl)($\eta_4$-butadiene)zirconium;
dimethylsilanediylbis(2-methyl-indenyl)($\eta_4$-butadiene)zirconium;
dimethylsilanediylbisindenyl($\eta_4$-butadiene)zirconium;
dimethylsilanediylbis(2-methylbenzindenyl)($\eta_4$-butadienezirconium;
dimethylsilanediyl(2-methylbenzindenyl)(2-methyl-indenyl)($\eta_4$-butadiene)zirconium;
dimethylsilanediyl(2-methylbenzindenyl)(2-methyl-4-phenylindenyl)($\eta_4$-butadiene)zirconium;
dimethylsilanediyl(2-methylindenyl)(4-phenylindenyl)($\eta_4$-butadiene)zirconium;
dimethylsilanediylbis(2-methyl-4-phenylindenyl)($\eta_4$-butadiene)zirconium;
dimethylsilanediylbis(2-methyl-4,6-diisopropylindenyl)($\eta_4$-butadiene)zirconium;
dimethylsilanediylbis(2-methylindenyl)($\eta_4$-butadiene)zirconium;
dimethylsilanediylbisindenyl($\eta_4$-butadiene)zirconium;
dimethylsilanediylbis(2-methylbenzindenyl)($\eta_4$-butadiene)zirconium;
dimethylsilanediyl(2-methylbenzindenyl)(2-methylindenyl)($\eta_4$-butadiene)zirconium;
dimethylsilanediyl(2-methylbenzindenyl)(2-methyl-4-phenylindenyl)($\eta_4$-butadiene)zirconium;
dimethylsilanediyl(2-benzindenyl)(4-phenylindenyl)($\eta_4$-butadiene)zirconium;
dimethylsilanediylbis(2-methyl-4-phenylindenyl)($\eta_4$-butadiene)zirconium;
dimethylsilanediylbis(2-methyl-4,6-diisopropylindenyl)($\eta_4$-butadiene)zirconium;
dimethylsilanediylbis(2-methyl-4-naphthylindenyl)($\eta_4$-butadiene)zirconium;
dimethylsilanediylbis(2-methylindenyl)($\eta_4$-butadiene)zirconium;
dimethylsilanediylbisindenyl($\eta_4$-butadiene)zirconium;
dimethylsilanediylbis(2-methylbenzindenyl)($\eta_4$-butadiene)zirconium;
dimethylsilanediyl(2-methylbenzindenyl)(2-methylindenyl)($\eta_4$-butadiene)zirconium;
dimethylsilanediyl(2-methylbenzindenyl)(2-methyl-4-phenylindenyl)($\eta_4$-butadiene)zirconium;
dimethylsilanediyl(2-methylbenzindenyl)(4-phenylindenyl)($\eta_4$-butadiene)zirconium;
dimethylsilanediylbis(2-methyl-4-phenylindenyl)($\eta_4$-butadiene)zirconium;
dimethylsilanediylbis(2-methyl-4,6-diisopropylindenyl)($\eta_4$-butadiene)zirconium;
dimethylsilanediylbis(2-methyl-4-naphthylindenyl)($\eta_4$-butadiene)zirconium;
methylphenylmethylene(fluorenyl)(cyclopentadienyl)($\eta_4$-butadiene)zirconium;
diphenylmethylene(fluorenyl)(cyclopentadienyl)($\eta_4$-butadiene)zirconium;
isopropylidene(3-methylcyclopentadienyl)(fluorenyl)($\eta_4$-butadiene)zirconium;
dimethylsilanediyl(3-tert-butylcyclopentadienyl)(fluorenyl)($\eta_4$-butadiene)zirconium;
diphenylsilanediyl(3-(trimethylsilyl)cyclopentadienyl)(fluorenyl)($\eta_4$-butadiene)zirconium;
phenylmethylsilanediylbis(2-methylindenyl)($\eta_4$-butadiene)zirconium;
phenylmethylsilanediylbisindenyl($\eta_4$-butadiene)zirconium;
phenylmethylsilanediylbis(2-methyl-4,5-benzindenyl)($\eta_4$-butadiene)zirconium;
phenylmethylsilanediyl(2-methyl-4,5-benzindenyl)(2-methylindenyl)($\eta_4$-butadiene)zirconium;
phenylmethylsilanediyl(2-methyl-4,5-benzindenyl)(2-methyl-4-phenylindenyl)($\eta_4$-butadiene)zirconium;
phenylmethylsilanediyl(2-methylindenyl)(4-phenylindenyl)($\eta_4$-butadiene)zirconium;

phenylmethylsilanediylbis(2-methyl-4-phenylindenyl)($\eta_4$-butadiene)zirconium;

phenylmethylsilanediylbis(2-ethyl-4-phenylindenyl)($\eta_4$-butadiene)zirconium;

phenylmethylsilanediylbis(2-methyl-4,6-diisopropylindenyl)($\eta_4$-butadiene)zirconium;

phenylmethylsilanediylbis(2-methyl-4-naphthylindenyl)($\eta_4$-butadiene)zirconium;

ethylenebis(2-methylindenyl)($\eta_4$-butadiene)zirconium;

ethylenebisindenyl($\eta_4$-butadiene)zirconium;

ethylenebis(2-methyl-4,5-benzindenyl)($\eta_4$-butadiene)zirconium;

ethylene(2-methyl-4,5-benzindenyl)(2-methyl-4-phenylindenyl)($\eta_4$-butadiene)zirconium;

ethylene(2-methylindenyl)(2-methyl-4-phenylindenyl)($\eta_4$-butadiene)zirconium;

ethylene(2-methylindenyl)(4-phenyl-indenyl)($\eta_4$-butadiene)zirconium;

ethylenebis(2-methyl-4,5-benzindenyl)($\eta_4$-butadiene)zirconium;

ethylenebis(2-methyl-4-phenylindenyl)($\eta_4$-butadiene)zirconium;

ethylenebis(2-methyl-4,6-diisopropylindenyl)($\eta_4$-butadiene)zirconium;

ethylenebis(2-methyl-4-naphthylindenyl)($\eta_4$-butadiene)zirconium;

ethylenebis(2-ethyl-4-phenylindenyl)($\eta_4$-butadiene)zirconium;

ethylenebis(2-ethyl-4,6-diisopropylindenyl)($\eta_4$-butadiene)zirconium;

ethylenebis(2-ethyl-4-naphthylindenyl)($\eta_4$-butadiene)zirconium;

dimethylsilanediylbis(2-ethyl-4-phenylindenyl)($\eta_4$-butadiene)zirconium;

dimethylsilanediylbis(2,3,5-trimethylcyclopentadienyl)($\eta_4$-butadiene)zirconium;

1,6-{bis[methylsilylbis(2-methyl-4-phenylindenyl($\eta_4$-butadiene)zirconium]}hexane;

1,6-{bis[methylsilylbis(2-ethyl-4-phenylindenyl($\eta_4$-butadiene)zirconium]}hexane;

1,6-{bis[methylsilylbis(2-methyl-4-naphthylindenyl($\eta_4$-butadiene)zirconium]}hexane;

1,6-{bis[methylsilylbis(2-methyl-4,5-benzindenyl($\eta_4$-butadiene)zirconium]}hexane;

1,6-{bis[methylsilyl(2-methyl-4-phenylindenyl)(2-methylindenyl($\eta_4$-butadiene)zirconium]}hexane;

1,2-{bis[methylsilylbis(2-methyl-4-phenylindenyl($\eta_4$-butadiene)zirconium]}ethane;

1,2-{bis[methylsilylbis(2-ethyl-4-phenylindenyl($\eta_4$-butadiene)zirconium]}ethane;

1,2-{bis[methylsilylbis(2-methyl-4-naphthylindenyl($\eta_4$-butadiene)zirconium]}ethane;

1,2-{bis[methylsilylbis(2-methyl-4,5-benzindenyl($\eta_4$-butadiene)zirconium)]}ethane; and, 1,2-{bis[methylsilyl(2-methyl-4-phenylindenyl)(2-methylindenyl)($\eta_4$-butadiene)zirconium]}ethane.

EXAMPLES

Hereinafter the present invention will be described with reference to EXAMPLES below but is not deemed to be limited thereto.

The following reaction was carried out in an argon or nitrogen atmosphere using the standard Schlenk technique. Solvents were provide for use after they were dried by refluxing in the presence of an appropriate drying agent and then distilling in an argon or nitrogen flow.

In the following EXAMPLES, the number average molecular weight (Mn) of polymers was determined by gel permeation chromatography, while the weight average molecular weight (Mw) was determined by elemental analysis.

Reference Example 1

Synthesis of 1,8-bis(p-Bromophenyl)-1,7-octadiyne p-Bromoiodobenzene (10 ml), 1,7-octadiyne, Pd(PPh$_3$)$_4$ (0.05 mmol), CuI (0.1 mmol) and tetrahydrofuran (hereinafter abbreviated as THF, 30 ml) were mixed in a Schlenk tube to give a solution. Triethylamine was added to the solution. The mixture was stirred at room temperature for 48 hours to proceed the reaction. The reaction was quenched with 3N hydrochloric acid. Next, the organic phase was extracted with diethyl ether followed by drying over anhydrous magnesium sulfate. The solvent was removed in vacuum to give a solid. The solid was washed with hexane to give the yellowish green solid in 75% yield.

$^1$H NMR (CDCl$_3$, Me$_4$Si) δ 1.75–1.78 (m, 4H), 2.44–2.47 (m, 4H), 7.23–7.26 (m, 4H), 7.39–7.42 (m, 4H); $^{13}$C NMR (CDCl$_3$, Me$_4$Si) δ 19.01 (2C), 27.73 (2C), 79.98 (2C), 91.00 (2C), 121.65 (2C), 122.86 (2C), 131.40 (4C), 132.99 (4C).

Example 1

2,5-bis(p-Bromophenyl)-cyclohexa[c]-1-zirconacyclopenta-2,4-diene

Bis-$\eta^5$-cylopentadienyl)dibutylzirconium (1.2 mmol) and THF (10 ml) were charged in a Schlenk tube. The solution was cooled to −78° C. and then n-butyl lithium (2.4 mmol) was added to the solution. The solution was allowed to stir at −78° C. for an hour. After 1,8-bis(p-bromophenyl)-1,7-octadiyne (1.0 mmol) was added to the reaction mixture at −78° C., the mixture was warmed to room temperature for an hour to give the title compound.

Example 2

1,4-bis(p-Bromophenyl)-2,3-dimethoxycarbonyl-5,6,7,8-tetrahydronaphthalene 2,5-Bis(p-bromophenyl)-cyclohexa[c]-1-zirconacyclopenta-2,4-diene obtained in EXAMPLE 1 was used in the solution state, without separating the diene. That is, dimethylacetylene dicarboxylate (TCI Inc., 2.5 mmol) and copper (I) chloride (2.5 mmol) were added at 0° C. to a THF (10 ml) solution of 2,5-bis(p-bromophenyl)-cyclohexa[c]-1-zirconacyclopenta-2,4-diene (1.0 mmol). The reaction mixture was warmed to room temperature followed by stirring for 6 hours. The reaction was quenched with 3N hydrochloric acid. Next, extraction was conducted with ether followed by drying over anhydrous magnesium sulfate. Column chromatography (hexane:diethyl ether=4:1) on silica gel gave the title compound in 80% yield.

$^1$H NMR (CDCl$_3$, Me$_4$Si) δ 1.64–1.65 (m, 4H), 2.40–2.42 (m, 4H), 3.47 (s, 6H), 7.08–7.10 (m, 4H), 7.53–7.55 (m, 4H); $^{13}$C NMR (CDCl$_3$, Me$_4$Si) δ 22.32 (2C), 29.06 (2C), 52.12 (2C), 121.65 (2C), 129.72 (2C), 130.69 (4C), 131.32 (4C), 137.54 (2C), 138.64 (2C), 138.72 (2C), 168.19 (2C). High resolution mass spectrum (HRMS) for C$_{26}$H$_{22}$O$_4$Br$_2$: calcd. 555.9883; found 555.9873.

The reactions occurred in REFERENCE EXAMPLE 1 to EXAMPLE 2 are summarized below.

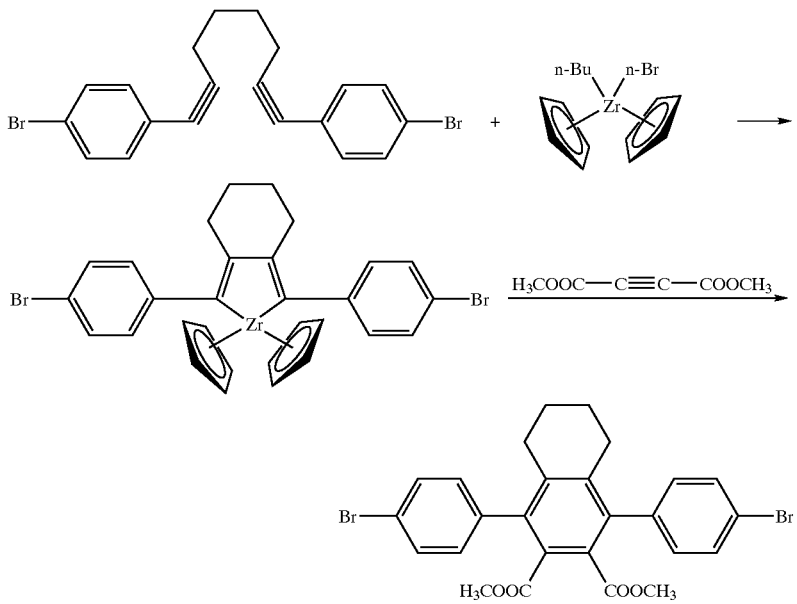

Example 3

Poly(1,4-phenylene-2',3'-dimethoxycarbonyl-5',6',7', 8'-tetrahydronaphthalene-1',4'-diyl-1'',4''-phenylene)

In a 20 ml Schlenk tube, bistriphenylphosphine dichloronickel (II) (0.05 mmol), bipyridine (0.05 mmol), metallic zinc (1.5 mmol) and 1,4-bis(p-bromophenyl)-2,3-dimethoxycarbonyl-5,6,7,8-teetrahydronaphthalene were charged. Next, dry dimethylformamide (5 ml) was added to the mixture followed by stirring for 3 hours at 80° C. A large amount of 3N hydrochloric acid and methanol were added to the resulting mixture to terminate the reaction. The solid in the solution was filtered, washed with methanol, diethyl ether and methanol, and dried in vacuum at 80° C. for 12 hours. The polymer was obtained as yellowish green solids in 75% yield.

According to gel permeation chromatography, the number average molecular weight (Mn) was 6870 and Mw/Mn was 1.7.

When the reaction was carried out at 80° C. for 24 hours instead of the reaction at 80° C. for 3 hours, the number average molecular weight (Mn) was 7510 and Mw/Mn was 1.8, according to gel permeation chromatography.

Example 4

2,5-bis(p-Bromophenyl)-cyclopenta[c]-1-zirconacyclopenta-2,4-diene

Bis($\eta^5$-cyclopentadienyl)dibutylzirconium (1.2 mmol) and THF (10 ml) were charged in a Schlenk tube. The solution was cooled to −78° C. and then n-butyl lithium (2.4 mmol) was added to the solution. The solution was allowed to stir at −78° C. for an hour. After 1,7-bis(p-bromophenyl)-1,6-heptadiyne (1.0 mmol) was added to the reaction mixture at −78° C., the resulting mixture was warmed to room temperature for an hour to give the title compound.

Example 5

4,7-bis(p-Bromophenyl)-5,6-dimethoxycarbonylindan

To a solution of 2,5-bis(p-bromophenyl)-cyclopenta[c]-1-zirconacyclopenta-2,4-diene (1.0 mmol) in THF (10 ml), dimethylacetylene dicarboxylate (TCI Inc., 2.5 mmol) and bistriphenylphosphine dibromonickel (II), $NiBr_2(PPh_3)_2$ (2.5 mmol) were added at 0° C. The reaction mixture was warmed to room temperature followed by stirring for 6 hours. The reaction was quenched with 3N hydrochloric acid. Next, extraction was conducted with ether followed by drying over anhydrous magnesium sulfate. Column chromatography (hexane:diethyl ether=4:1) on silica gel gave the title compound.

$^1$H NMR (CDCl$_3$, Me$_4$Si) δ 1.96–2.03 (m, 2H), 2.77 (t, J=7.4 Hz, 4H), 3.54 (s, 6H), 7.14 (d, J=8.2 Hz, 4H), 7.54 (d, J=8.2 Hz, 4H). $^{13}$C NMR (CDCl$_3$, Me$_4$Si) δ 24.79, 32.93 (2C), 52.20 (2C), 121.70 (2C), 130.12 (4C), 130.78 (2C), 131.30 (4C), 135.29 (2C), (2C), 137.40 (2C), 145.78 (2C), 168.26 (2C). High resolution mass spectrum (HRMS) for $C_{25}H_{20}O_4Br_2$:

| calcd.: | C, 55.17; | H, 3.70; | Br, 29.36 |
| found: | C, 55.34; | H, 3.89; | Br, 29.07 |

Example 6

Poly(1,4-phenylene-5',6'-dimethoxycarbonylindan-4',7'-diyl-1'',4''-phenylene)

Next, bistriphenylphosphine dichloronickel (II) (0.05 mmol), bipyridine (0.05 mmol), metallic zinc (1.5 mmol) and teraryl were charged in a 20 ml Schlenk tube, obtained in EXAMPLE 5. Next, dry dimethylformamide (5 ml) was added to the mixture followed by stirring for 3 hours or 24 hours at 80° C. A large amount of 3N hydrochloric acid and methanol were added to the resulting mixture to terminate the reaction. The solid in the solution was filtered, washed with methanol, diethyl ether and methanol, and dried in vacuum at 80° C. for 12 hours to give the polyarylene in 48% yield.

The results are shown in TABLE 1.

TABLE 1

|  | Yield (%) | Mn | Mw | Mw/Mn |
|---|---|---|---|---|
| 3 hours | 82 | 4750 | 5750 | 1.2 |
| 24 hours | 85 | 4810 | 5850 | 1.2 |

Example 7

2,5-bis(p-Bromophenyl)-cyclofurana[c]-1-zirconacyclopenta-2,4-diene

Bis($\eta^5$-cyclopentadienyl)dibutylzirconium (1.2 mmol) and THF (10 ml) were charged in a Schlenk tube. The solution was cooled to −78° C. and then n-butyl lithium (2.4 mmol) was added to the solution. The solution was stirred at −78° C. for an hour. After 1,7-bis(p-bromophenyl)-4-oxa-1,6-heptadiyne, namely, di(3-(p-bromophenyl)-2-propynyl) ether (1.0 mmol) was added to the reaction mixture at −78° C., the mixture was warmed to room temperature for an hour to give the title compound.

That is, the title compound is one of the compounds represented by formula (V) described above, in which $R^1$ and $R^2$ are combined together to form a group shown by formula: —$CH_2$—$CH_2$—O—$CH_2$—$CH_2$—, and the 5-membered ring intervened by the oxygen atom is condensed with zirconacyclopentadiene.

Example 8

4,7-Bis(p-Bromophenyl)-5,6-dimethoxycarbonyl-1,3-dihydroisobenzofuran

To a solution of the compound obtained in EXAMPLE 7 in THF (10 ml), dimethylacetylene dicarboxylate (TCI Inc., 2.5 mmol), bistriphenylphosphine dibromonickel (II) and $NiBr_2(PPh_3)_2$ (2.5 mmol) were added at 0° C. The reaction mixture was warmed to room temperature followed by stirring for 12 hours. The reaction was quenched with 3N hydrochloric acid. Next, extraction was conducted with ether followed by drying over anhydrous magnesium sulfate. Column chromatography (hexane:diethyl ether=4:1) on silica gel gave the title compound in 65% yield.

$^1$H NMR (CDCl$_3$, Me$_4$Si) δ 3.58 (s, 6H), 4.98 (s, 4H), 7.15 (d, J=8.2 Hz), 7.56 (d, J=8.2 Hz). $^{13}$C NMR (CDCl$_3$, Me$_4$Si) δ 52.48(2C), 73.73 (2C), 122.52 (2C), 129.59 (4C), 131.77 (4C), 132.28 (2C), 133.17 (2C), 136.06 (2C), 140.96 (2C), 167.66 (2C).

Example 9

Poly(1,4-phenylene-5',6'-dimethoxycarbonyl-1',3'-dihydroisobenzofuran-4',7'-diyl-1",4"-phenylene)

In a 20 ml Schlenk tube obtained in EXAMPLE 8, bistriphenylphosphine dichloronickel (II) (0.05 mmol), bipyridine (0.05 mmol), metallic zinc (1.5 mmol) and the teraryl were charged. Next, dry dimethylformamide (5 ml) was added to the mixture followed by stirring for 3 hours or 24 hours at 80° C. A large amount of 3N hydrochloric acid and methanol were added to the resulting mixture to terminate the reaction. The solid in the solution was filtered, washed with methanol, diethyl ether and methanol, and dried in vacuum at 80° C. for 12 hours to give the polyarylene in 74% yield.

The molecular weight was found to be 6700 by elemental analysis.

Example 10

Mixture of
2,4-bis(p-bromophenyl)-3,5-dibutyl-1-zirconacyclopenta-2,4-diene, 2,5-bis(p-bromophenyl)-3,4-dibutyl-1-zirconacyclopenta-2,4-diene and 3,4-bis(p-bromophenyl)-2,5-dibutyl-1-zirconacyclopenta-2,4-diene:

Bis($\eta^5$-cyclopentadienyl)dibutylzirconium (1.2 mmol) and THF (10 ml) were charged in a Schlenk tube. The solution was cooled to −78° C. and then n-butyl lithium (2.4 mmol) was added to the solution. The solution was allowed to stir at −78° C. for an hour. After 1-(p-bromophenyl)-1-hexyne (1.0 mmol) was added to the reaction mixture at −78° C., the resulting mixture was warmed to room temperature for an hour to give a mixture of 2,4-bis(p-bromophenyl)-3,5-dibutyl-1-zirconacyclopenta-2,4-diene (5 parts by weight), 2,5-bis(p-bromophenyl)-3,4-dibutyl-1-zirconacyclopenta-2,4-diene (1 part by weight) and 3,4-bis(p-bromophenyl)-2,5-dibutyl-1-zirconacyclopenta-2,4-diene (1 part by weight).

In this EXAMPLE, the three isomers of the zirconacyclopenta-2,4-diene derivatives are not separated. However, these derivatives can be separated from each other by chromatography, if desired, followed by recrystallization.

Example 11

Mixture of
1,5-bis(p-bromophenyl)-2,3-dimethoxycarbonyl-4,6-dibutylbenzene,
1,4-bis(p-bromophenyl)-2,3-dimethoxycarbonyl-5,6-dibutylbenzene and
1,2-bis(p-bromophenyl)-4,5-dimethoxycarbonyl-3,6-dibutylbenzene.

To a solution of the mixture obtained in EXAMPLE 10 in THF (10 ml), dimethylacetylene dicarboxylate (TCI Inc., 2.5 mmol) and copper (I) chloride (2.5 mmol) were added at 0° C. The reaction mixture was warmed to room temperature followed by stirring for 6 hours. The reaction was quenched with 3N hydrochloric acid. Next, extraction was performed with ether followed by drying over anhydrous magnesium sulfate. Column chromatography (hexane:diethyl ether=4:1) was performed on silica gel gave the mixture of three kinds of monomers (5:1:1) in 80% yield.

1,5-bis(p-Bromophenyl)-2,3-dimethoxycarbonyl-4,6-dibutylbenzene $^1$H NMR (CDCl$_3$, Me$_4$Si) δ 0.43 (t, J=7.3 Hz, 3H), 0.69 (t, J=7.4 Hz, 3H), 0.75–0.85 (m, 2H), 0.95–1.05 (m, 2H), 1.06–1.20 (m, 2H), 1.25–1.40 (m, 2H), 2.00–2.20 (m, 2H), 2.40–2.55 (m, 2H), 3.47 (s, 3H), 3.84 (s, 3H), 7.08 (d, J=8.3 Hz, 2H), 7.14 (d, J=8.2 Hz, 2H), 7.50 (d, J=8.4 Hz, 2H), 7.57 (d, J=8.2 Hz, 2H). $^{13}$C NMR (CDCl$_3$, Me$_4$Si) δ 12.79, 13.22, 22.26, 22.55, 30.56, 30.61, 32.06, 33.08, 51.79, 52.15, 121.23, 121.36, 129.27, 130.67 (2C), 130.96 (2C), 130.99 (2C), 131.06 (2C), 132.77, 136.47, 137.26, 137.77, 139.32, 142.09, 142.89, 168.14, 168.37.

1,4-bis(p-Bromophenyl)-2,3-dimethoxycarbonyl-5,6-dibutylbenzene $^1$H NMR (CDCl$_3$, Me$_4$Si) δ 0.66 (t, J=7.2 Hz, 6H), 0.75–0.85 (m, 4H), 1.06–1.20 (m, 4H), 2.40–2.50 (m, 4H), 3.44 (s, 6H), 6.81 (d, J=8.2 Hz, 4H), 7.27(d, J=8.3 Hz, 4H). $^{13}$C NMR (CDCl$_3$, Me$_4$Si) δ 13.20 (2C), 22.48 (2C), 29.62 (2C), 30.45 (2C), 51.70 (2C), 120.63 (2C), 130.20 (2C), 130.98 (4C), 131.21 (4C), 137.59 (2C), 142.09 (2C), 142.70 (2C), 168.60(2C).

1,2-bis(p-Bromophenyl)-4,5-dimethoxycarbonyl-3,6-dibutylbenzene $^1$H NMR (CDCl$_3$, Me$_4$Si) δ 0.72 (t, J=7.3 Hz, 6H), 0.96–1.06 (m, 4H), 1.25–1.40 (m, 4H), 2.45–2.55 (m, 4H), 3.89 (s, 6H), 7.16 (d, J=8.0 Hz, 4H), 7.53 (d, J=8.3 Hz, 4H). $^{13}$C NMR (CDCl$_3$, Me$_4$Si) δ 13.20 (2C), 22.68 (2C), 30.38 (2C), 32.72 (2C), 52.1 (2C), 121.41 (2C), 130.49 (4C), 130.90 (4C), 131.85 (2C), 136.99 (2C), 138.62 (2C), 142.09 (2C), 168.64 (2C). High resolution mass spectrum (HRMS) of the mixture for C$_{26}$H$_{22}$O$_4$Br$_2$: calcd.: 555.9883; found: 555.9873.

In this EXAMPLE, the three kinds of monomers are not separated. However, these monomers can be separated from each other by chromatography or the like. In particular, 1,5-bis(p-bromophenyl)-2,3-dimethoxycarbonyl-4,6-dibutylbenzene, which is predominantly formed, can be readily isolated from the other isomers.

Example 12

Poly(1,4-phenylene-2',3'-dimethoxycarbonyl-dibutylphenylene-1",4"-phenylene)

In a 20 ml Schlenk tube, bistriphenylphosphine dichloronickel (II) (0.05 mmol), bipyridine (0.05 mmol), metallic zinc (1.5 mmol) and the mixture of three kinds of monomers obtained in EXAMPLE 11 were charged. Next, dry dimethylformamide (5 ml) was added to the mixture followed by stirring for 3 hours or 24 hours at 80° C. A large amount of 3N hydrochloric acid and methanol were added to the resulting mixture to terminate the reaction. The solid in the solution was filtered, washed with methanol, diethyl ether and methanol, and dried in vacuum at 80° C. for 12 hours. The polymer was obtained as yellowish green solids in 75% yield.

TABLE 2

|  | Yield (%) | Mn | Mw | Mw/Mn |
|---|---|---|---|---|
| 3 hours | 78 | 5370 | 6760 | 1.3 |
| 24 hours | 80 | 5150 | 6480 | 1.3 |

Example 13

The reaction was carried out in a manner similar to EXAMPLE 5 to give the teraryl and, the teraryl was reacted in a manner similar to EXAMPLE 6 to give the polyarylene, except that the following acetylene derivatives were used in place of dimethylacetylene dicarboxylate in EXAMPLE 5.

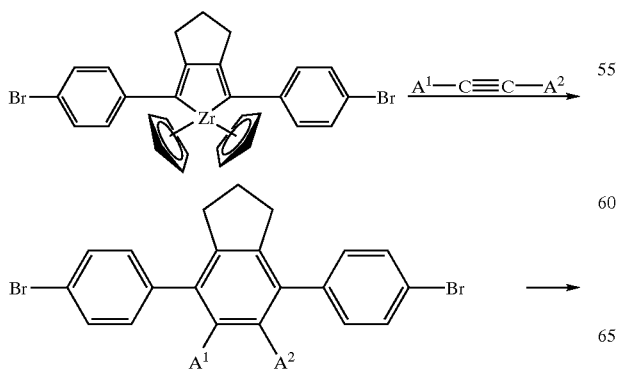

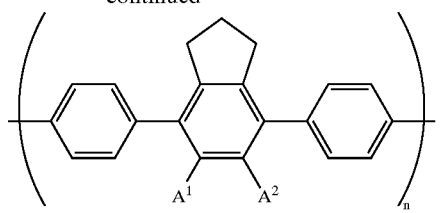

(wherein A$^1$ and A$^2$ are as given in the table below and n is an integer of 2 or more.)

TABLE 3

| No. | A1 | A2 |
|---|---|---|
| 1 | Pr | Pr |
| 2 | Et | Et |
| 3 | Pr | H |
| 4 | Ph | H |
| 5 | EtO | H |
| 6 | Ph | COOEt |
| 7 | Et | COMe |

The polyarylenes of the present invention find extensive explications as electrically conductive resins. The polyarylenes can be used also as resin compositions in a variety of formed shapes.

What is claimed is:

1. A polyarylene comprising a recurring unit of formula (I) or (II) below:

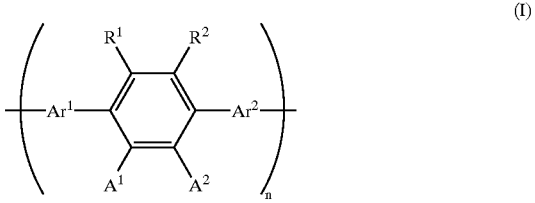

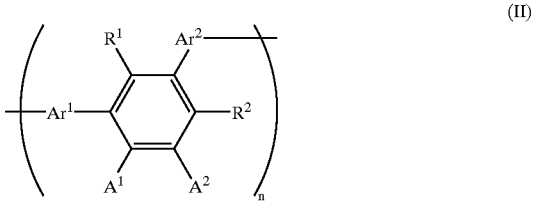

(wherein:
Ar$^1$ and Ar$^2$, which may be the same or different, each represents independently an arylene having 4 to 18 carbon atoms, which may be substituted and may contain 1 to 5 nitrogen atoms;

R$^1$ and R$^2$, which may be the same or different, each represents independently a C$_1$–C$_{20}$ hydrocarbon group which may be substituted, a C$_1$–C$_{20}$ alkoxy group which may be substituted, a C$_6$–C$_{20}$aryloxy group which may be substituted, an amine group, hydroxy group or a group shown by formula: —Si(R$^3$)(R$^4$)(R$^5$) (wherein R$^3$, R$^4$ and R$^5$, which may be the same or different, each represents independently a C$_1$–C$_{20}$ alkyl group, a C$_6$–C$_{20}$ arylalkyl group, a C$_1$–C$_{20}$ alkoxy group or a C$_6$–C$_{20}$ arylalkyloxy group);

provided that, in the recurring unit of formula (I), R$^1$ and R$^2$ may form together a C$_4$–C$_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; a $C_1$–$C_{20}$ alkoxycarbonyl group which may be substituted; a $C_6$–$C_{20}$ aryloxycarbonyl group which may be substituted; cyano group (—CN); carbamoyl group (—C(=O)NH$_2$); a haloformyl group (—C(=O)—X, wherein X is a halogen atom); or formyl group (—C(=O)—H); and, n is an integer of 2 or more).

2. The polyarylene according to claim 1, wherein each of $Ar^1$ and $Ar^2$, which may be the same or different, represents independently a phenylene group which may be substituted.

3. The polyarylene according to claim 1, which has the recurring unit shown by formula (I), wherein $R^1$ and $R^2$ form together a $C_4$–$C_{20}$ saturated or unsaturated ring which may be intervened by an oxygen atom and may be substituted.

4. The polyarylene according to claim 1, wherein the $C_1$–$C_{20}$ hydrocarbon group is a linear or branched $C_1$–$C_{20}$ alkyl group, a linear or branched $C_2$–$C_{20}$ alkenyl group, a linear or branched $C_2$–$C_{20}$ alkynyl group, a linear or branched $C_3$–$C_{20}$ allyl group, a linear or branched $C_4$–$C_{20}$ alkadienyl group, a linear or branched $C_4$–$C_{20}$ polyenyl group, a $C_6$–$C_{18}$ aryl group, a $C_6$–$C_{20}$ alkylaryl group, a $C_6$–$C_{20}$ arylalkyl group, a $C_4$–$C_{20}$ cycloalkyl group, or a $C_4$–$C_{20}$ cycloalkenyl group.

5. A resin composition comprising the polyarylene according to claim 1 and a synthetic organic polymer.

6. A teraryl represented by formula (III) or (IV) below:

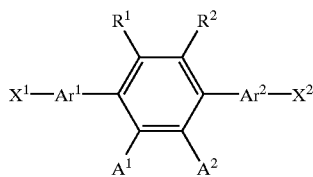

(III)

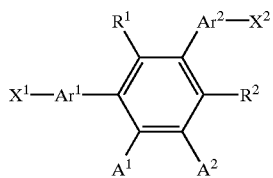

(IV)

(wherein:

$Ar^1$ and $Ar^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group)

provided that, in the recurring unit of formula (III), $R^1$ and $R^2$ may form together a $C_4$–$C_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; a $C_1$–$C_{20}$ alkoxycarbonyl group which may be substituted; a $C_6$–$C_{20}$ aryloxycarbonyl group which may be substituted; cyano group (—CN); carbamoyl group (—C(=O)NH$_2$); a haloformyl group (—C(=O)—X, wherein X is a halogen atom); or formyl group (—C(=O)—H); and, $X^1$ and $X^2$, which may be the same or different, each represents independently a leaving group).

7. A process for producing a polyarylene, which comprises polymerizing a teraryl represented by formula (III) or (IV) below:

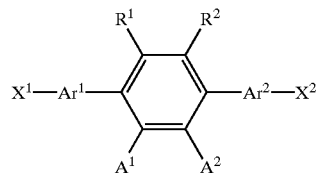

(III)

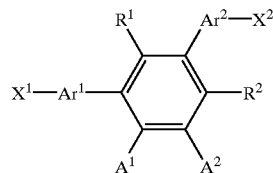

(IV)

(wherein:

$Ar^1$ and $Ar^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the recurring unit of formula (III), $R^1$ and $R^2$ may form together a $C_4$–$C_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; a $C_1$–$C_{20}$ alkoxycarbonyl group which may be substituted; a $C_6$–$C_{20}$ aryloxycarbonyl group which may be substituted; cyano group (—CN); carbamoyl group (—C(=O)NH$_2$); a haloformyl group (—C(=O)—X, wherein X is a halogen atom); or formyl group (—C(=O)—H); and, $X^1$ and $X^2$, which may be the same or different, each represents independently a leaving group); to produce a polyarylene represented by formula (I) or (II) below:

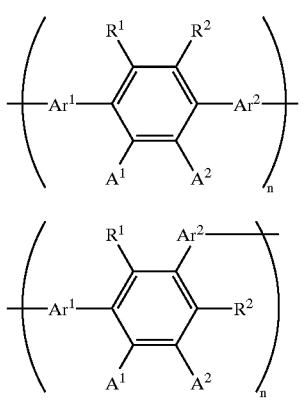

(wherein each of $Ar^1$, $Ar^2$, $R^1$, $R^2$, $A^1$ and $A^2$ has the same significance as defined above; and n is an integer of 2 or more).

8. A process for producing a polyarylene, which comprises reacting a metallacyclopentadiene represented by formula (V) or (VI) below:

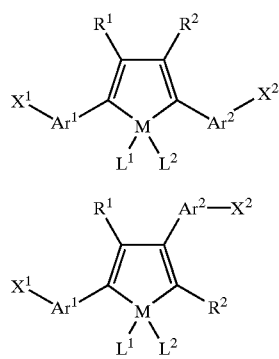

(wherein:
Ar$^1$ and Ar$^2$$_1$ which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the metallacyclopentadiene shown by formula (V), $R^1$ and $R^2$ may form together a $C_4$–$C_{20}$ saturated or unsaturated ring which may be intervened by an oxygen atom and may be substituted;

M is a metal from Groups III–V or the lanthanide series of the Periodic Table;

$L^1$ and $L^2$, which may be the same or different, each represents independently an anionic ligand, provided that $L^1$ and $L^2$ may be crosslinked; and, $X^1$ and $X^2$, which may be the same or different, each represents independently a leaving group);

with an alkyne derivative represented by formula (VII) below:

(wherein;
$A^{1a}$ and $A^{2a}$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; a $C_1$–$C_{20}$ alkoxycarbonyl group which may be substituted; a $C_6$–$C_{20}$ aryloxycarbonyl group which may be substituted; or cyano group (—CN)); to produce a teraryl represented by formula (IIIa) or (IVa) below:

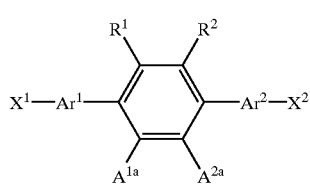

(wherein each of $Ar^1$, $Ar^2$, $R^1$, $R^2$ $A^{1a}$, $A^{2a}$, $X^1$ and $X^2$ has the same significance as defined above); and polymerizing the resulting teraryl to produce the polyarylene represented by formula (Ia) or (IIa) below:

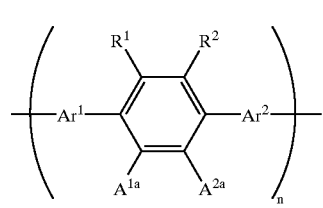

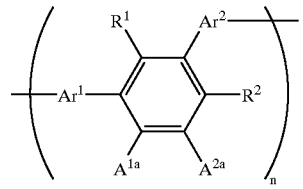

(wherein each of $Ar^1$, $Ar^2$, $R^2$, $R^2$, $A^{1a}$ and $A^{2a}$ has the same significance as defined above; and n is an integer of 2 or more).

9. A process for producing the polyarylene according to claim 8, wherein M is a metal from Group IV or the lanthanide series of the Periodic Table, and the anionic ligand is non-localized cyclic $\eta^5$-coordination type ligand, a $C_1$–$C_{20}$ alkoxy group, a $C_6$–$C_{20}$ aryloxy group or a dialkylamide group.

10. The process for producing the polyarylene according to claim 9, wherein the non-localized cyclic $\eta^5$-coordination type ligand is a cyclopentadienyl, indenyl, fluorenyl or azulenyl group, which may be substituted.

11. The process for producing the polyarylene according to claim 6, wherein the reaction proceeds in the presence of a compound containing a metal from Groups IX–XV of the Periodic Table.

12. A metallacyclopentadiene represented by formula (V) or (VI) below:

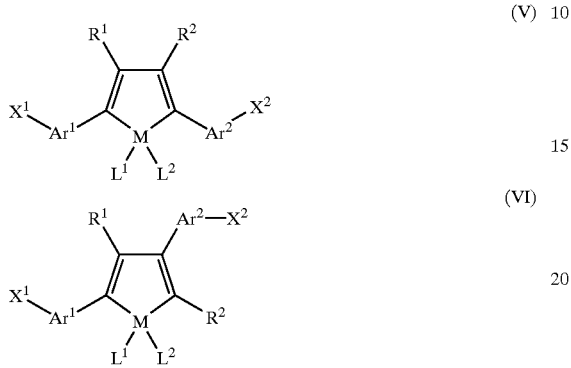

(wherein:
M is a metal from Groups III–V or the lanthanide series of the Periodic Table;

$L^1$ and $L^2$, which may be the same or different, each represents independently an anionic ligand, provided that $L^1$ and $L^2$ may be crosslinked;

$Ar^1$ and $Ar^2$, which may be the same or different, each represents independently an arylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the metallacyclopentadiene shown by formula (V), $R^1$ and $R^2$ may form together a $C_4$–$C_{20}$ saturated or unsaturated ring which may be intervened by an oxygen atom and may be substituted; and, $X^1$ and $X^2$, which may be the same or different, each represents independently a leaving group).

13. A polyarylene comprising a recurring unit represented by formula (I) below:

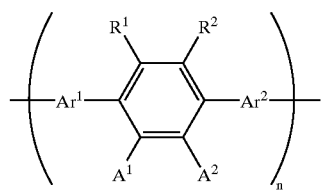

(wherein:

$Ar^1$ and $Ar^2$, which may be the same or different, each represents independently a paraarylene having 4 to 18 carbon atoms, which may be substituted and may contain 1 to 5 nitrogen atoms;

$R^1$ and $R^2$, which may be the same or different, each represents independently a $C_1$–$C_{20}$ hydrocarbon group which may be substituted, a $C_1$–$C_{20}$ alkoxy group which may be substituted, a $C_6$–$C_{20}$ aryloxy group which may be substituted, an amine group, hydroxy group or a group shown by formula: —Si($R^3$)($R^4$)($R^5$) (wherein $R^3$, $R^4$ and $R^5$, which may be the same or different, each represents independently a $C_1$–$C_{20}$ alkyl group, a $C_6$–$C_{20}$ arylalkyl group, a $C_1$–$C_{20}$ alkoxy group or a $C_6$–$C_{20}$ arylalkyloxy group);

provided that, in the recurring unit of formula (I), $R^1$ and $R^2$ may form together a $C_4$–$C_{20}$ saturated or unsaturated ring which may be intervened by an oxygen atom and may be substituted;

$A^1$ and $A^2$, which may be the same or different, each represents independently hydrogen atom; a $C_1$–$C_{20}$ hydrocarbon group which may be substituted; a $C_1$–$C_{20}$ alkoxy group which may be substituted; a $C_6$–$C_{20}$ aryloxy group which may be substituted; a $C_6$–$C_{20}$ alkylaryloxy group which may be substituted; an alkoxycarbonyl group which may be substituted; a $C_6$–$C_{20}$ aryloxycarbonyl group which may be substituted; cyano group (—CN); carbamoyl group (—C(=O)NH$_2$); a haloformyl group (—C(=O)—X, wherein X is a halogen atom); or formyl group (—C(=O)—H); and, n is an integer of 2 or more).

14. The polyarylene according to claim 13, wherein each of $Ar^1$ and $Ar^2$, which may be the same or different, represents independently a paraphenylene group which may be substituted.

15. The polyarylene according to claim 13, which has the recurring unit shown by formula (I) above, wherein $R^1$ and $R^2$ form together a $C_4$–$C_{20}$ saturated or unsaturated ring which may be intervened by an oxygen atom and may be substituted.

16. The polyarylene according to claim 13, wherein the $C_1$–$C_{20}$ hydrocarbon group is a linear or branched $C_1$–$C_{20}$ alkyl group, a linear or branched $C_2$–$C_{20}$ alkenyl group, a linear or branched $C_2$–$C_{20}$ alkynyl group, a linear or branched $C_3$–$C_{20}$ allyl group, a linear or branched $C_4$–$C_{20}$ alkadienyl group, a linear or branched $C_4$–$C_{20}$ polyenyl group, a $C_6$–$C_{18}$ aryl group, a $C_6$–$C_{20}$ alkylaryl group, a $C_6$–$C_{20}$ arylalkyl group, a $C_4$–$C_{20}$ cycloalkyl group, or a $C_4$–$C_{20}$ cycloalkenyl group.

17. A resin composition comprising the polyarylene according to claim 13 and a synthetic organic polymer.

18. The process for producing the polyarylene according to claim 7, wherein the reaction proceeds in the presence of a compound containing a metal from Groups IX–XV of the Periodic Table.

19. The process for producing the polyarylene according to claim 8, wherein the reaction proceeds in the presence of a compound containing a metal from Groups IX–XV of the Periodic Table.

* * * * *